United States Patent
Jarosiewicz

(10) Patent No.: US 12,303,694 B2
(45) Date of Patent: *May 20, 2025

(54) METHODS AND SYSTEMS FOR OPTIMIZING THERAPY USING STIMULATION MIMICKING NATURAL SEIZURES

(71) Applicant: NeuroPace, Inc., Mountain View, CA (US)

(72) Inventor: Beata Jarosiewicz, San Jose, CA (US)

(73) Assignee: NeuroPace, Inc., Mountain View, CA (US)

( * ) Notice: Subject to any disclaimer, the term of this patent is extended or adjusted under 35 U.S.C. 154(b) by 143 days.

This patent is subject to a terminal disclaimer.

(21) Appl. No.: 18/110,676

(22) Filed: Feb. 16, 2023

(65) Prior Publication Data
US 2023/0201599 A1  Jun. 29, 2023

Related U.S. Application Data

(63) Continuation of application No. 16/803,945, filed on Feb. 27, 2020, now Pat. No. 11,612,750.

(Continued)

(51) Int. Cl.
*A61N 1/36* (2006.01)
*G06F 16/2458* (2019.01)
(Continued)

(52) U.S. Cl.
CPC ..... *A61N 1/36139* (2013.01); *A61N 1/36175* (2013.01); *G06F 16/2474* (2019.01);
(Continued)

(58) Field of Classification Search
CPC ........ A61B 2560/0219; A61B 2562/04; A61B 2562/046; A61B 5/0022; A61B 5/0031;
(Continued)

(56) References Cited

U.S. PATENT DOCUMENTS 6,016,449 A   1/2000  Fischell et al.
6,480,743 B1  11/2002  Kirkpatrick et al.
(Continued)

FOREIGN PATENT DOCUMENTS

WO   2016154298   9/2016

OTHER PUBLICATIONS

Ng et al., "Why are seizures rare in rapid eye movement sleep? Review of the frequency of seizures in different sleep stages," M. Epilepsy Res. Treat.,2013:932790 (2013).

(Continued)

*Primary Examiner* — George Manuel
(74) *Attorney, Agent, or Firm* — LOZA & LOZA, LLP; David S. Sarisky

(57) ABSTRACT

Systems, methods, and devices for automatic generation of a stimulation therapy that mimics electrographic activity in the brain at natural seizure termination define a stimulation therapy to be generated by an implanted component of a medical device system and delivered to a subject through identifying data characterizing a patient's seizures, especially at termination. A machine learning model identifies the seizures or seizure types from which to establish a canonical seizure or seizure type, and an algorithm translates the canonical seizure or seizure type into data that can be used to characterize a stimulation therapy. The systems, methods, and devices, include those configured to deliver the stimulation therapy that emulates the canonical seizure or seizure type when the seizure is detected, with the aim of terminating the seizure sooner than it would terminate without intervention.

19 Claims, 20 Drawing Sheets
(3 of 20 Drawing Sheet(s) Filed in Color)

Related U.S. Application Data

(60) Provisional application No. 62/820,753, filed on Mar. 19, 2019.

(51) Int. Cl.

| | |
|---|---|
| *G06N 5/04* | (2023.01) |
| *G06N 20/00* | (2019.01) |
| *G16H 30/20* | (2018.01) |
| *G16H 50/50* | (2018.01) |
| *A61B 5/00* | (2006.01) |
| *A61N 1/05* | (2006.01) |

(52) U.S. Cl.
CPC ............... *G06N 5/04* (2013.01); *G06N 20/00* (2019.01); *G16H 30/20* (2018.01); *G16H 50/50* (2018.01); *A61B 5/4094* (2013.01); *A61B 5/7282* (2013.01); *A61N 1/0531* (2013.01); *A61N 1/0534* (2013.01)

(58) Field of Classification Search
CPC ......... A61B 5/01; A61B 5/02; A61B 5/14542; A61B 5/293; A61B 5/296; A61B 5/4064; A61B 5/4082; A61B 5/4094; A61B 5/4812; A61B 5/4836; A61B 5/7214; A61B 5/7257; A61B 5/7267; A61B 5/7282; A61N 1/0531; A61N 1/0534; A61N 1/36139; A61N 1/3615; A61N 1/36171; A61N 1/36175; G06F 16/2474; G06N 20/00; G06N 3/044; G06N 3/045; G06N 3/047; G06N 3/08; G06N 5/04; G06N 7/01; G16H 20/30; G16H 30/20; G16H 40/63; G16H 50/20; G16H 50/50
See application file for complete search history.

(56) References Cited

U.S. PATENT DOCUMENTS

| | | |
|---|---|---|
| 6,594,524 B2 | 7/2003 | Esteller et al. |
| 6,810,285 B2 | 10/2004 | Pless et al. |
| 7,209,787 B2 | 4/2007 | Dilorenzo |
| 7,231,254 B2 | 6/2007 | Dilorenzo |
| 7,242,984 B2 | 7/2007 | Dilorenzo |
| 7,277,758 B2 | 10/2007 | Dilorenzo |
| 7,280,867 B2 | 10/2007 | Frei et al. |
| 7,324,851 B1 | 1/2008 | Dilorenzo |
| 7,403,820 B2 | 7/2008 | Dilorenzo |
| 7,529,582 B1 | 5/2009 | Dilorenzo |
| 7,542,803 B2 | 6/2009 | Heruth et al. |
| 7,599,736 B2 | 10/2009 | Dilorenzo |
| 7,623,928 B2 | 11/2009 | Dilorenzo |
| 7,676,273 B2 | 3/2010 | Goetz et al. |
| 7,747,325 B2 | 6/2010 | Dilorenzo |
| 7,822,481 B2 | 10/2010 | Gerber et al. |
| 7,853,322 B2 | 12/2010 | Bourget et al. |
| 7,853,329 B2 | 12/2010 | Dilorenzo |
| 7,894,903 B2 | 2/2011 | John |
| 7,899,545 B2 | 3/2011 | John |
| 7,930,035 B2 | 4/2011 | Dilorenzo |
| 7,957,797 B2 | 6/2011 | Bourget et al. |
| 7,957,809 B2 | 6/2011 | Bourget et al. |
| 7,966,073 B2 | 6/2011 | Pless et al. |
| 7,974,696 B1 | 7/2011 | Dilorenzo |
| 8,027,730 B2 | 9/2011 | John |
| 8,126,567 B2 | 2/2012 | Gerber et al. |
| 8,543,214 B2 | 9/2013 | Osorio et al. |
| 8,543,217 B2 | 9/2013 | Stone et al. |
| 8,694,115 B2 | 4/2014 | Goetz et al. |
| 8,706,237 B2 | 4/2014 | Giftakis et al. |
| 8,731,656 B2 | 5/2014 | Bourget et al. |
| 8,903,486 B2 | 12/2014 | Bourget et al. |
| 9,931,508 B2 | 4/2018 | Burdick et al. |
| 9,955,921 B2 | 5/2018 | Esteller et al. |
| 10,123,717 B2 | 11/2018 | Tcheng |
| 10,252,056 B2 | 4/2019 | Mogul |
| 2003/0018367 A1 | 1/2003 | Dilorenzo |
| 2003/0171789 A1 | 9/2003 | Malek et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0267330 A1 | 12/2004 | Lee et al. |
| 2005/0021103 A1 | 1/2005 | Dilorenzo |
| 2005/0021104 A1 | 1/2005 | Dilorenzo |
| 2005/0060007 A1 | 3/2005 | Goetz |
| 2005/0060008 A1 | 3/2005 | Goetz |
| 2006/0089924 A1 | 4/2006 | Raskutti et al. |
| 2006/0265022 A1 | 11/2006 | John et al. |
| 2007/0073355 A1 | 3/2007 | Dilorenzo |
| 2007/0142862 A1 | 6/2007 | Dilorenzo |
| 2007/0142874 A1 | 6/2007 | John |
| 2007/0162086 A1 | 7/2007 | Dilorenzo |
| 2007/0167991 A1 | 7/2007 | Dilorenzo |
| 2007/0208212 A1 | 9/2007 | Dilorenzo |
| 2007/0287931 A1 | 12/2007 | Dilorenzo |
| 2008/0058773 A1 | 3/2008 | John |
| 2008/0061961 A1 | 3/2008 | John |
| 2008/0071314 A1 | 3/2008 | John |
| 2008/0109005 A1 | 5/2008 | Trudeau et al. |
| 2008/0119900 A1 | 5/2008 | Dilorenzo |
| 2009/0018609 A1 | 1/2009 | Dilorenzo |
| 2010/0023089 A1 | 1/2010 | Dilorenzo |
| 2010/0217348 A1 | 8/2010 | Dilorenzo |
| 2010/0241183 A1 | 9/2010 | Dilorenzo |
| 2010/0249859 A1 | 9/2010 | Dilorenzo |
| 2011/0040353 A1 | 2/2011 | Gerber et al. |
| 2011/0307030 A1 | 12/2011 | John |
| 2012/0289869 A1 | 11/2012 | Tyler |
| 2016/0228705 A1 | 8/2016 | Crowder et al. |
| 2017/0136240 A1* | 5/2017 | Mogul ............... A61N 1/36064 |
| 2018/0300576 A1 | 10/2018 | Dalyac et al. |
| 2019/0065996 A1 | 2/2019 | Matsuki |

OTHER PUBLICATIONS

Ogren et al., "Three-dimensional hippocampal atrophy maps distinguish two common temporal lobe seizure-onset patterns," Epilepsia, 50(6):1361-1370 (2009).

Osorio et al., "Real-Time Automated Detection and Quantitative Analysis of Seizures and Short-Term Prediction of Clinical Onset", Epilepsia, 39(6):615-627 (1998).

Perucca et al., "Intracranial electroencephalographic seizure-onset patterns: effect of underlying pathology," J. Brain: 137:183-196 (2014).

Popovych et al., "Desynchronizing electrical and sensory coordinated reset neuromodulation", Frontiers in Human Neuroscience, Mar. 20, 2012, vol. 6, Article 58.

Schiller et al., "Characterization and comparison of local onset and remote propagated electrographic seizures recorded with intracranial electrodes," Epilepsia,39:380-388 (1998).

Skarpaas et al., "Clinical and electrocorticographic response to antiepileptic drugs in patients treated with responsive stimulation", Epilepsy & Behavior 83, 192-200, (2018).

Tass et al., "Long-lasting desynchronization in rat hippocampal slice induced by coordinated reset stimulation", Physical Review F 80, 011902 (2009).

Tass et al., "Coordinated reset has sustained aftereffects in Parkinsonian monkeys," Ann.Neurol,72:816-820 (2012).

Uriguen et al., "Comparison of background EEG activity of different groups of patients with idiopathic epilepsy using Shannon spectral entropy and cluster-based permutation statistical testing". PLoS One 12, (Sep. 18, 2017).

Van Putten et al., "Detecting temporal lobe seizures from scalp EEG recordings: a comparison of various features," Clin. Neurophysiol.,116:2480-2489 (2005).

Vaswani et al., "Attention is all you need". Advances in Neural Information Processing Systems 30 (2017).

Wackermann, "Beyond mapping: estimating complexity of multichannel EEG recordings," Acta Neurobiol. Exp. (Wars.),56:197-208 (1996).

(56) References Cited

OTHER PUBLICATIONS

Shoeb et al., "Application of Machine Learning to Epileptic Seizure Detection", Appearing in the Proceedings of the 27th International Conference on Machine Learning, Haifa, Israel 2010, Copyright 2010.
Spencer et al., "Morphological patterns of seizures recorded intracranially," 33:537-545 (1992).
Lee et al., "Intracranial EEG seizure-onset patterns in neocortical epilepsy," 41:297-307 (2000).
Langan et al., "Case-control study of SUDEP," Neurology,64:1131-1133 (2005).
Bateman et al., "Serotonin reuptake inhibitors are associated with reduced severity of ictal hypoxemia in medically refractory partial epilepsy," 51:2211-2214 (2010).
Shoeb, Thesis "Application of Machine Learning to Epileptic Seizure Onset Detection and Treatment", Submitted to Harvard-MIT Div. of Health Sciences re Dr. of Philosophy in EE and Med Engineering at MIT, Sep. 2009.
D'Alessandro et al., "A multi-feature and multi-channel univariate selection process for seizure prediction", Clinical Neurophysiology 116 (2005) 506-516.
Conradsen et al., "Automated algorithm for generalised tonic-clonic epileptic seizure onset detection based on sEMG zero-crossing rate", IEEE Transactions on Biomedical Engineering, Copyright IEEE 2011, pubs-permissions@ieee.org.
Kharbouch et al., "An algorithm for seizure onset detection using intracranial EEG," Epilepsy Balmy. Dec. 2011; 22(01): S29-S35.
Khan et al., "Automatic Detection of Seizure Onset in Pediatric EEG", International Journal of Embedded Systems and Applications (IJESA) vol. 2, No. 3, Sep. 2012.
Zhang et al., "An automatic patient-specific seizure onset detection method in intracranial EEG based on incremental nonlinear dimensionality reduction", Computers in Biology and Medicine 40 (2010) 889-899. Automated Detection and Quantitative Analysis of Seizures and Short-Term Prediction of Clinical Onset, Epilepsia, 39(6):615-627 (1998).
Gabor et al., "Automated Seizure Detection Using a Self-Organizing Neural Network", Dept. of Neurology, University of CA, Davis Medical Center, Jan. 5, 1996; Published Apr. 15, 1996, Electroencephalography and Clinical Neurophysiology 99 (1996) 257-266.
Gabor, "Seizure Detection Using a Self-Organizing Neural Network: Validation and Comparison with Other Detection Strategies", Dept. of Neurology, University of CA, Davis Medical Center, Accepted for Publication Feb. 28, 1998, Electroencephalography and Clinical Neurophysiology 107 (1998) 27-32.
Russakovsky et al., "ImageNet Large Scale Visual Recognition Challenge", International Journal of Computer Vision, available online Apr. 11, 2015, published Dec. 2015; vol. 115, Issue 3, DOI 10.1007/s11263-015-0816-; pp. 211-252.
Lecun et al., "Deep Learning", Nature, May 27, 2015, vol. 521; DOI:10.1038/nature14539; pp. 436-444.
Xu et al., "Survey of Clustering Algorithms", IEEE Transactions on Neural Networks, vol. 16, No. 3, May 1, 2005; 35 pages.
Krizhevsky et al., "ImageNet Classification with Deep Convolutional Neural Networks", NIPS'12 Proceedings of the 25th International Conference on Neural Information Processing Systems—vol. 1, pp. 1097-1105, Dec. 3, 2012.
Desai, "Insights from mining large-scale human EcoG data", ICTAL2017, The Penumbra Conference, presented Aug. 21, 2017; 9 pages.
Esteva et al. "Dermatologist level classification of skin cancer with deep neural networks", Nature, vol. 542, published Feb. 2, 2017, pp. 115-118.
Desai et al., "Transfer-learning for differentiating epileptic patients who respond to treatment based on chronic ambulatory ECoG data," in 2019 9th International IEEE/EMBS Conference on Neural Engineering (NER), 2019: IEEE, pp. 1-4.
Hussein et al., "Epileptic Seizure Detection: A Deep Learning Approach", ArXiv:1803.09848v1, Mar. 27, 2018, pp. 1-12; 2018.

Tsiouris et al., "A Long Short-Term Memory deep learning network for the prediction of epileptic seizures using EEG signals", Computers in Biology and Medicine, vol. 99, Aug. 1, 2018, pp. 24-37.
Thodoroff et al., "Learning Robust Features using Deep Learning for Automatic Seizure Detection", ArXiv:1608.00220, Jul. 31, 2016, pp. 1-12.
Pailla et al., "Autoencoders for learning template spectrograms in electrocorticographic signals", Journal of Neural Engineering, vol. 16, No. 1, Jan. 14, 2019.
Ling et al., "Waveform Modeling and Generation Using Hierarchical Recurrent Neural Networks for Speech Bandwidth Extension", IEEE/ACM Transactions on Audio, Speech, and Language Processing, vol. 26, No. 5, pp. 883-894, May 2018.
Zeiler et al., "Visualizing and Understanding Convolutional Networks", ArXiv:1311.2901v3, Nov. 28, 2013, pp. 1-11.
Desai et al. "Evaluation of potential epilepsy biomarkers in long-term electrocorticographic activity", Abstracts, Nov. 21, 2016, www.aesnet.org, 3 pages.
Baud et al., "Multi-day rhythms modulate seizure risk in epilepsy." Nat Commun 9, 88, (2018).
Brinkmann et al., "Forecasting Seizures Using Intracranial EEG Measures and SVM in Naturally Occurring Canine Epilepsy," G. A. PLoS.One., 10:e0133900 (2015).
Cantero et al., "Sleep-dependent theta oscillations in the human hippocampus and neocortex,", J Neurosci,23:10897-10903 (2003).
Carrington et al.,"Effect of focal low-frequency stimulation on amygdala-kindled afterdischarge thresholds and seizure profiles in fast- and slow-kindling rat strains," Epilepsia,48:1604-1613 (2007).
Chan et al., "Automated seizure onset detection for accurate onset time determination in intracranial EEG," Clin. Neurophysiol.,119:2687-2696 (2008).
Colom, "Septal networks: relevance to theta rhythm, epilepsy and Alzheimer's disease," J Neurochem., 96:609-623 (2006).
Crespel et al., "Sleep influence on seizures and epilepsy effects on sleep in partial frontal and temporal lobe epilepsies," M. Clin. Neurophysiol.,111 Suppl 2:S54-S59 (2000).
Desai et al., "Deep Learning for seizure classification and potential seizure biomarker discovery", Abstract, published online at www.aesnet.org on Nov. 20, 2017; 2 pages.
Desai et al., "Quantitative electrocorticographic biomarkers of clinical outcomes in mesial temporal lobe epileptic patients treated with the RNS system", Clinical Neurophysiology 130, 1364-1374, (2019).
García-Hernández et al., "Septo-hippocampal networks in chronic epilepsy", EAT Neurol. Mar. 2010; 222(1):86-92.
Goodman et al., "Preemptive low-frequency stimulation decreases the incidence of amygdala-kindled seizures," Epilepsia,46:1-7 (2005).
Herman et al., "Distribution of partial seizures during the sleep—wake cycle: differences by seizure onset site," Neurology,56:1453-1459 (2001).
Karoly et al., "The circadian profile of epilepsy improves seizure forecasting." Brain 140, 2169-2182, (2017).
Desai et al. "Recurrent Neural Networks for Forecasting Epileptiform Electrographic Activity 24 Hours in Advance", Abstracts, Nov. 6, 2018, www.aesnet.org, 3 pages.
Kisilev et al., "Medical Image Description Using Multi-task-loss CNN." Deep Learning and Data Labeling for Medical Applications. Dlmia Labels 2016 2016. Lecture Notes in Computer Science( ), vol. 10008. Springer, Cham. https://doi.org/10.1007/978-3-319-46976-8_13.
Litt et al., "Epileptic Seizures May Begin Hours in Advance of Clinical Onset: A Report of Five Patients", Neuron, vol. 30, 51-64, Apr. 2001.
Logesparan et al., "Optimal features for online seizure detection", Medical & Biological Engineering & Computing, 50.7 (2012): 659-669, and Supplementary Material relating to article.
Lysyansky et al., "Optimal number of stimulation contacts for coordinated reset neuromodulation," Front Neuroeng.,6:5 (2013).
Malow, "The interaction between sleep and epilepsy," Epilepsia,48 Suppl 9:36-38 (2007).
Welsh et al., "A circadian rhythm of hippocampal theta activity in the mouse," Physiol.Behav,35:533-538 (1985).

(56) References Cited

OTHER PUBLICATIONS

Meisel et al., "Intrinsic excitability measures track antiepileptic drug action and uncover increasing/ decreasing excitability over the wake/sleep cycle". Proc Natl Acad Sci U S A 112, 14694-14699, (Nov. 6, 2015).
Miller et al., "Anticonvulsant effects of the experimental induction of hippocampal theta activity," Epilepsy Res.,18:195-204 (1994).
Minecan et al., "Relationship of epileptic seizures to sleep stage and sleep depth," Sleep,25:899-904 (2002).

* cited by examiner

METHODS AND SYSTEMS FOR OPTIMIZING THERAPY USING STIMULATION MIMICKING NATURAL SEIZURES

CROSS-REFERENCE TO RELATED APPLICATION

This application is a continuation of U.S. application Ser. No. 16/803,945, filed on Feb. 27, 2020, now U.S. Pat. No. 11,612,750, entitled "Methods and Systems for Optimizing Therapy Using Stimulation Mimicking Natural Seizures," which is claims the benefit of and priority to U.S. Provisional Patent Application Ser. No. 62/820,753, filed Mar. 19, 2019, for "Methods and Systems for Optimizing Therapy Using Stimulation Mimicking Natural Seizures," the entire disclosures of which are incorporated herein by reference.

TECHNICAL FIELD

The present disclosure relates generally to devices and systems for seizure therapy, and more particularly, to methods and systems for optimizing seizure therapy using stimulation therapies derived from characteristics and features of natural seizures.

BACKGROUND

Epilepsy, a neurological disorder characterized by repeated seizures (specifically, abnormal brain activity causing episodic impairment or loss of consciousness, abnormal motor phenomena, psychic or sensory disturbances, or the perturbation of the autonomic nervous system), is debilitating to a great number of people. It is believed that as many as two to four million Americans suffer from various forms of epilepsy. Its prevalence worldwide may be in excess of one hundred million.

Because epilepsy is characterized by seizures, its sufferers are often limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

Available treatments for neurological disorders generally, and epilepsy in particular, include drugs, resective or ablative surgery, and devices, including implantable neurostimulators.

The medications used in pharmacological therapy can have significant side effects, including toxicity, and patient compliance with a drug regimen can be an issue. In addition, some seizures do not respond to drugs.

Resective or ablative surgery involves removing or destroying brain tissue. Sometimes this is not an option, if a patient's seizures are suspected to arise from an eloquent area of the brain (i.e., an area of the brain that, if removed or destroyed, may result in significant disability). In addition, sometimes seizures re-occur even after such surgery, in adjacent or other areas of the brain.

Devices are known that can deliver a form of electrical stimulation to brain tissue in an effort to modulate the neural response. There are implantable devices that can be configured to stimulate the vagus nerve or a deep brain structure periodically, for example, on a scheduled basis. A responsive direct brain neurostimulator (RNS System, NeuroPace, Inc. (Mountain View, CA)) can be configured to detect unusual or abnormal activity in electrographic signals sensed from leads on a surface of the brain or brain depth lead and then to deliver a therapy of electrical stimulation in response to the detecting conditions which individually or collectively define an "event" relative to that abnormal activity. An abnormal event may correspond to features of the electrographic signal that are believed to be associated with interictal epileptiform activity or the onset of an electrographic seizure (as compared to normal background electrographic activity).

In responsive stimulation, there are many possible parameters to program both with respect to what to detect and what to deliver as therapy, and each parameter may have a wide range of possible values. Thus, it is possible to tailor detection and therapy for each individual patient. However, determining which parameters and/or parameter values to use to optimize patient outcomes can be complex. Although current electrical stimulation treatments have been beneficial, further developments and improvements are desired.

SUMMARY

One aspect of the present disclosure relates to a method for defining a neuromodulation therapy based on a characterization of what the end of a seizure is like electrographically. The stimulation to be generated and delivered with an implanted medical device relies on identifying data characterizing a termination of a patient's seizure. In some embodiments, each seizure corresponds to an episode of electrographic activity that is different from and which disrupts the patient's background electrographic activity, and in some embodiments, each seizure can be characterized by an onset (beginning), an evolution (middle), and an offset or termination (end). The method can include training a machine learning model with a training set of data characterizing a first plurality of seizures relating to a subject to identify a seizure termination for that patient's seizures and applying the trained machine learning model to identify seizure terminations from data characterizing a second plurality of seizures. The method can include generating a canonical seizure termination from the identified seizure terminations, the canonical seizure termination being a pattern represented in an electrographic signal, applying the electrographic signal to an analyzer, and determining with the analyzer a waveform shape that characterizes the pattern. The method can include generating with the analyzer a stimulation therapy that approximates the waveform shape.

In some embodiments, the data characterizing the first plurality of seizures includes either raw time-series data or a spectrogram of raw time-series data. In some embodiments, the time-series data for each seizure includes at least one channel of data recorded as a local field potential (voltage between two electrodes over time). In some embodiments, where data are recorded from multiple channels, each channel corresponds to data recorded from a different pair of recording sites (electrodes) than every other channel.

In some embodiments, the first plurality of electrographic seizures include primarily seizures which transitioned from onset, to evolution, to termination naturally as well as some seizures which were treated with a stimulation therapy as an intervention while they were occurring, but the stimulation failed to abort them. In some embodiments, the pattern comprising the canonical seizure termination can be a single pattern representative of multiple seizure terminations identified from the data characterizing the seizures.

In some embodiments, generating the single pattern comprising the canonical seizure termination includes selecting multiple seizure terminations identified from the data characterizing the seizures, time-aligning the selected multiple seizure terminations, and generating average data for the time-aligned selected multiple seizure terminations. In some embodiments, the selected multiple seizure terminations are time-aligned via dynamic time warping. In some embodiments, the multiple seizure terminations include all of the seizure terminations identified from the data characterizing the seizures.

In some embodiments, generating the single pattern comprising the canonical seizure termination includes selecting multiple seizure terminations identified from the data characterizing the second plurality of seizures, generating a high-level feature space representation of the multiple seizure terminations, and identifying the high-level feature space representation as the single pattern. In some embodiments, determining a waveform shape that characterizes the pattern includes comparing the waveform to a threshold and creating pulse characterization data that defines at least one pulse for each portion of the waveform that exceeds the threshold.

In some embodiments, the pulse characterization data identifies an amplitude for each specified pulse. In some embodiments, the method includes selecting a portion of the waveform exceeding the threshold, comparing the selected portion of the waveform to the threshold, and determining a difference between the selected portion of the waveform and the threshold. In some embodiments, the amplitude of the at least one pulse associated with the selected portion of the waveform varies proportionally to the difference between the threshold and the selected portion of the waveform exceeding the threshold. In some embodiments, the method includes identifying an amplitude for each portion of time-series data exceeding the threshold, and selecting an amplitude for pulses associated with the pulse characterization data, which selected amplitude for the pulses corresponds to the identified amplitude of the time-series data associated with each of the pulses.

In some embodiments, the pulses are biphasic pulses. In some embodiments, the pulse characterization data specifies a pulse width for each pulse identified in the pulse characterization data. In some embodiments, the pulse width of each pulse varies according to a duration of the portion of the waveform associated with that pulse and that exceeds the threshold.

In some embodiments, the method includes dividing the seizure terminations into at least a first group and a second group. In some embodiments, generating a canonical seizure termination from the identified seizure terminations includes generating a first canonical seizure termination for the first group and generating a second canonical seizure termination for the second group. In some embodiments, the seizure terminations are divided based on attributes of the electrographic seizure associated with each of the seizure terminations. In some embodiments, the attributes of the electrographic seizures include attributes of the seizure preceding the seizure termination. In some embodiments, the method includes updating software of a neurostimulator with the stimulation therapy.

One aspect of the present disclosure relates to a method of treating a patient's seizures with electrical stimulation. In some embodiments, the seizure represents an episode of electrographic activity that is different from and which disrupts background electrographic activity. The seizure can be characterized by an onset, an evolution, and an offset or termination. The method includes modeling a plurality of seizures to identify a canonical seizure offset pattern corresponding to the plurality of seizures, creating a stimulation therapy that emulates the canonical seizure offset pattern, monitoring a patient's individual electrographic activity for seizures, and responding to detection of a seizure with the stimulation therapy.

In some embodiments, modeling a plurality of seizures to identify a canonical seizure offset pattern includes identifying at least a first seizure type and a second seizure type, modeling a first plurality of seizures corresponding to the first seizure type to identify a first canonical seizure offset, and modeling a second plurality of seizures corresponding to the second seizure type to identify a second canonical seizure offset. In some embodiments, creating a stimulation therapy that emulates the seizure offset includes creating a first stimulation therapy that emulates the first seizure offset, and creating a second stimulation therapy that emulates the second seizure offset.

In some embodiments, the method includes detecting a seizure, and determining a type for the seizure. In some embodiments, responding to detection of the seizure with the stimulation therapy includes responding to detection of the seizure with the stimulation therapy corresponding to the determined type of the seizure.

In some embodiments, modeling the plurality of seizures includes training a machine learning model with a plurality of samples of the seizures obtained from the patient. In some embodiments, the machine learning model is one of a deep learning model or a recurrent neural network. In some embodiments, the recurrent neural network can be a long short term memory neural network. In some embodiments, monitoring a patient's individual electrographic activity for seizures includes monitoring for a seizure onset. In some embodiments, responding to a seizure with the stimulation therapy includes responding to detection of the seizure onset.

In some embodiments, the canonical seizure offset corresponds to time-series data derived by time-aligning the seizures using dynamic time warping and then averaging (or taking the median or mode of) the time-aligned seizures. In some embodiments, creating a stimulation therapy to emulate the canonical seizure offset further includes creating pulse characterization data based on the canonical seizure offset. In some embodiments, responding to detection of a seizure with the stimulation therapy includes translating the pulse characterization data into a train of stimulation pulses and then delivering the train of stimulation pulses to the patient. In some embodiments, creating a stimulation therapy that emulates the canonical seizure offset further includes discretizing the canonical seizure offset, comparing the discretized canonical seizure offset to a threshold, and creating pulse characterization data specifying pulses for portions of the discretized canonical seizure offset exceeding the threshold. In some embodiments, each specified pulse is a biphasic stimulation pulse. In some embodiments, an amplitude of each specified pulse varies according to an amplitude of an associated portion of the discretized canonical seizure offset exceeding the threshold.

One aspect of the present disclosure relates to a system for delivering a stimulation therapy to a portion of a human brain in response to detection of a seizure. The system includes implantable components and external components. The implantable components include a neurostimulator and one or more electrode-bearing brain leads. When connected to the neurostimulator, the leads can both sense electrical activity from neural tissue and deliver electrical stimulation to neural tissue via the electrodes. A control module of the neurostimulator processes sensed signals and analyzes them to detect pre-determined features or patterns when they occur. In some embodiments, the control module is configured to detect features or a pattern corresponding to an onset of a seizure, select a stimulation therapy with which to respond to detection of the onset pattern, and deliver the stimulation therapy via the electrodes. The system can include a processor to model a plurality of seizures based on signals sensed by the electrodes to identify a canonical seizure offset corresponding to the plurality of seizures, create a stimulation therapy that emulates the canonical seizure offset, and provide the stimulation therapy to the control module. When the neurostimulator detects an onset pattern, it can deliver the stimulation therapy in response.

In some embodiments, identifying canonical seizure terminations or offsets can occur in the neurostimulator, externally of the neurostimulator, or some combination of internally and externally of the neurostimulator. In some embodiments, modeling a plurality of seizures to identify a canonical seizure offset includes identifying at least a first seizure type and a second seizure type, modeling a first plurality of seizures corresponding to the first seizure type to identify a first canonical seizure offset, and modeling a second plurality of seizures corresponding to the second seizure type to identify a second canonical seizure offset. In other embodiments, more than two different seizure types may be identified for an individual based on analysis of the individual's seizures, and each seizure type would have its own corresponding canonical seizure offset.

In some embodiments, creating a stimulation therapy to emulate the seizure offset includes creating a first stimulation therapy to emulate the first seizure offset and creating a second stimulation therapy to emulate the second seizure offset. In some embodiments, the neurostimulator can detect a seizure and determine a seizure type for what it detects. In some embodiments, selecting the stimulation therapy in response to the detection of a seizure onset includes selecting the stimulation therapy which corresponds to the determined seizure type. In some embodiments, delivering the stimulation therapy includes delivering the selected stimulation therapy via the electrodes.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

Various aspects of devices and systems for seizure therapy will now be presented in the detailed description by way of example, and not by way of limitation, with reference to the accompanying drawings, wherein.

DETAILED DESCRIPTION

Figure 1:
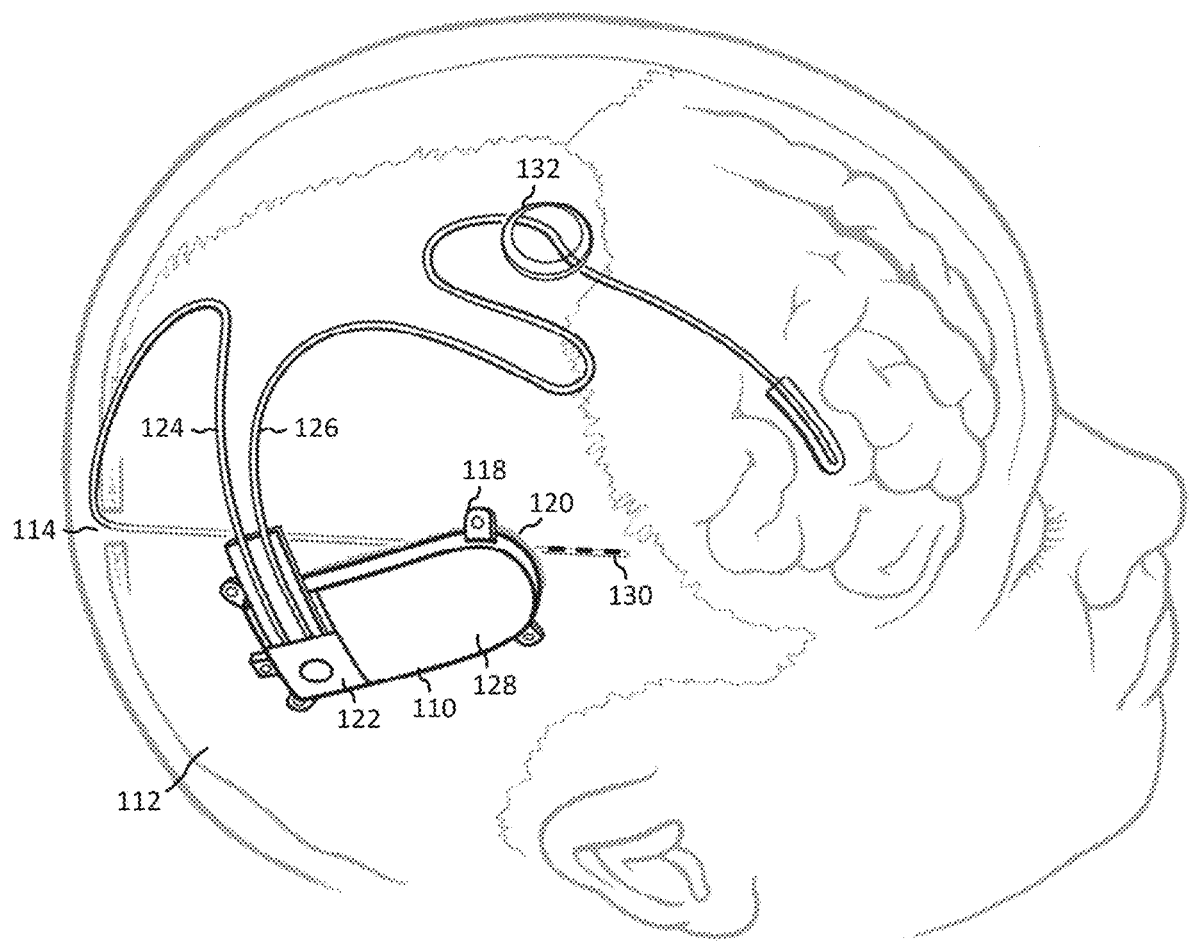
FIG. 1 is a perspective schematic view of a patient's cranium showing the placement of a neurostimulator, including leads extending to the patient's brain.

Neuromodulation in the form of electrical stimulation is currently used to treat epilepsy. For example, the RNS® System by NeuroPace, Inc. (Mountain View, CA) includes implantable components (a programmable neurostimulator and electrode-bearing brain leads) and external components (a patient remote monitor, a physician programmer, and a database and database applications (clinician user interfaces). Each lead is implanted in the patient so that the electrodes are at or near a suspected focus of abnormal brain activity believed to be associated with the patient's seizures ("seizure focus"). The neurostimulator is connected to the leads and also implanted intracranially in the patient. The physician can use the programmer to program the values of a variety of parameters which define (1) what the neurostimulator detects as abnormal brain activity (e.g., what it detects as electrographic seizures) in the signals sensed through the leads; and (2) what the neurostimulator delivers as therapy, in the form of electrical stimulation, through the leads in response to detecting the abnormal brain activity. The RNS System offers several tools that can be configured with programmable parameters to define which patterns or events are detected as triggers for stimulation. The stimulation the RNS System is configurable to deliver is biphasic pulsatile stimulation, and the programmable parameters that define it include current (or voltage) amplitude, pulse width, pulse frequency, burst composition (nature and type of pulses comprising a burst of pulses), stimulation pathway across the various available electrodes, and burst duration.

Every individual's epilepsy is unique, and thus having a lot of options for programming the neurostimulator allows therapy to be customized for each patient both in terms of what features in the sensed signals are detected as abnormal events and in terms of which waveforms are delivered in an effort to terminate the abnormal brain activity or to otherwise reduce the severity and/or the frequency of the patient's clinical seizures. However, some trial and error is often involved in choosing what to use as a trigger for stimulation and then what form of stimulation to deliver. And even when the physician has made those choices, translating the choices into which specific parameters to use and what values to select for each can be a daunting task, at least for the reason that it takes time. Making programming decisions for an individual based on what has worked well for other patients who have something in common with the individual often reduces the time to therapy optimization. For example, a starting "recipe" of programming parameters/parameter values may be based, in part, on the individual being a member of a class of patients whose epilepsy is believed to originate from a particular region of the brain (e.g., the patients all may share a seizure focus in the mesial temporal lobe), so the user may choose to use the same configuration of electrodes (or "montage") to detect activity or to deliver stimulation for these patients. Or a class of patients may comprise individuals whose abnormal brain signals or electrographic seizures begin in a similar way (i.e., similar types of "seizure onsets"), so the user may choose to use a form of stimulation for an individual in this class that is known to have worked well with other patients with the same type of seizure onset. Choosing to program an individual's RNS System based on what has worked well for other patients whose epilepsy has something in common with the individual is effective much of the time, but not always.

Seizures are often referred to as clinical seizures and electrographic seizures. More specifically, the term "clinical seizure" is typically used to refer to a seizure that has an observable (or subjectively detectable) consequence for the person. An "electrographic seizure" is one that is recorded by electrodes placed in the brain, which may or may not have a clinical consequence for the person. Reference herein to a "seizure" is a reference to an "electrographic seizure", unless the term "clinical seizure" is used.

An electrographic seizure that fully develops and terminates naturally or other than as a direct result of an electrical stimulation intervention typically can be characterized by a beginning or an "onset", an evolution, and a termination or "offset". (Experience with the RNS System has afforded access to a great deal of electrographic data chronically recorded from a great many patients receiving the RNS Therapy. These data include electrographic seizures that have terminated without any electrical stimulation having been applied as an intervention as well as electrographic seizures for which electrical stimulation was applied but was not obviously the cause of the eventual termination of the seizures. For simplicity, a seizure which terminates "naturally", as used herein, includes any seizure that appears to have terminated on its own and not as an immediate consequence of electrical stimulation.) Thus, a patient's seizures may be characterized herein as having terminated naturally, even when the patient is receiving therapies such as electrical stimulation and/or anti-epileptic drugs.

A seizure can be identified based on electrographic signals sensed from a patient. These signals can be sensed via one or several electrodes coupled to portions of the patient's brain and then conditioned and processed by an implanted device such as a neurostimulator. In some embodiments, a seizure can be identified as described in U.S. Pat. No. 6,810,285, filed on Jun. 28, 2001, and entitled "Seizure Sensing and Detection Using an Implantable Device," and in U.S. Publication No. 2016/0228705, filed on Feb. 10, 2016, and entitled "Seizure Onset Classification and Stimulation Pattern Selection," the entirety of each of which is hereby incorporated by reference herein.

Using responsive direct brain stimulation to determine which form of electrical stimulation to deliver to a patient and when to deliver it have proven effective in treating epilepsy in many patients (clinical investigations of the RNS System have shown that ~70% of patients experience a reduction of at least 50% in seizure rate when stimulation parameters are configured in a similar way with values within the same ranges, i.e., using a "standard" set of stimulation parameters or a recommended recipe of stimulation parameters). But further improvements are always desirable to optimize patient outcomes. When effective, stimulation therapy may (1) terminate a seizure shortly after onset, preventing it from fully developing or evolving, (2) reduce the severity of the seizures (so that the patient experiences fewer clinical symptoms), or (3) result in the patient having seizures less often. However, configuring stimulation based on the characteristics of the individual's own seizures, as contrasted to configuring it based just on what has worked well for others, may give short shrift to the particular characteristics of the person's electrographic seizures. Because epilepsy manifests differently in each individual, it is possible that more individualized, data-driven stimulation could lead to improved clinical outcomes (e.g., freedom from seizures).

As noted, seizures can be classified in various ways, both across patients and within an individual (e.g., by onset location or the attributes at onset/onset type). Of particular interest here are the attributes of an individual's seizures at termination or offset, and a standard way of representing those seizure terminations so they can be leveraged in defining an effective stimulation therapy for the individual. The terms "seizure termination" and "seizure offset" are used interchangeably herein, and refer to the last part of a seizure, typically the last several seconds, where the electrographic activity characteristic of the seizure in the brain area or areas that is seizing is transitioning from the peak of the seizure back to normal (baseline) brain activity. The duration of seizure termination may vary depending on the type or severity of seizure and may range from a fraction of a second to tens of seconds.

Through use of methods and systems disclosed herein, a waveform to be delivered as an electrical stimulation therapy can be generated based on a canonical seizure termination determined for an individual, such that when that waveform is delivered to the patient as an intervention at the beginning of a seizure or while the seizure is evolving, the stimulation therapy will terminate the seizure immediately, or at least sooner than it otherwise would have terminated without the stimulation intervention.

Specifically, methods, devices, and/or systems disclosed herein can define an electrical stimulation therapy that is generated and delivered by a system including some implantable components, namely, a neurostimulator and electrodes with which the neurostimulator is coupled, as through one or more brain leads. These methods, devices, and/or systems include identifying patterns characterizing periods corresponding to termination of some or all of a patient's electrographic seizures. These electrographic seizures can include an "onset" (or simply a beginning), an evolution or development, and a termination, also referred to herein as an "offset" (or simply an end).

As part of identifying the attributes which characterize a patient's seizure terminations, a machine learning model is trained with what have been identified for it as a patient's seizure terminations, and then the trained machine learning model can operate on other sets of data for the patient to further identify seizure terminations. Depending on how much variation there is among a given patient's seizures, the patient's seizure terminations are used to generate either one or a plurality of canonical seizure terminations. A stimulation therapy is generated for each canonical seizure termination that matches or approximates one or several attributes of the canonical seizure termination. (Desirably, the seizure terminations selected for/by the algorithm are natural seizure terminations inasmuch as each seizure progresses from onset, evolution, to offset either (i) with no electrical intervention having been applied at all; or (ii) with any applied electrical intervention having been unsuccessful in terminating the seizure any earlier than about half way through the seizure.) The methods, devices, and/or systems can include programming the neurostimulator so that when it detects the onset of a seizure in the patient in signals sensed from the electrodes, it will generate and deliver to the patient through the electrodes a stimulation therapy designed to mimic the attributes of an appropriate one of the canonical seizure terminations. The hope and expectation is that the stimulation therapy will quickly terminate the patient's seizure, either right at onset or before it fully develops or evolves.

The methods, devices, and/or systems, and others disclosed herein can be used to create a custom stimulation therapy or therapies for a patient based on that patient's seizure terminations. The stimulation therapy(ies) may be applied as a first intervention option or as an alternative intervention option when some other option (such as a standard set of stimulation parameters or a starting 'recipe' yield less than optimal outcomes). Each custom stimulation therapy can be associated with one or several attributes of a given seizure group, such that when a seizure is detected in a patient, the seizure can be classified as belonging to the group with which it shares common attributes, and the custom stimulation therapy associated with that group can be selected, generated, and provided to the patient.

FIG. 1 shows an implantable neurostimulator 110 according to embodiments, which is designed to be implanted intracranially in a patient (under the scalp, in a defect formed in the cranium (craniectomy)). In an alternative embodiment, the neurostimulator 110 is implanted under the patient's scalp but external to and without breaching the cranium; it is expected, however, that this configuration would generally cause an undesirable protrusion in the patient's scalp where the neurostimulator is located. In yet another alternative embodiment, when it is not possible to implant the neurostimulator intracranially, it may be implanted pectorally (not shown), with leads extending through the patient's neck and between the patient's cranium and scalp, as necessary.

The neurostimulator 110 described and illustrated herein is preferably a responsive neurostimulator for detecting and treating epilepsy by detecting seizures or their onsets or precursors, and for preventing and/or terminating such epileptic seizures. As the term is used herein, a responsive direct brain neurostimulator is a device capable of detecting or predicting ictal activity (or other neurological events) and providing electrical stimulation to neural tissue in response to that activity, where the electrical stimulation is specifically intended to terminate the ictal activity, treat a neurological event, prevent an unwanted neurological event from occurring, or lessen the severity or frequency of certain symptoms of a neurological disorder. As disclosed herein, the responsive neurostimulator detects ictal activity by systems and methods according to the invention. Ictal activity includes electrographic seizures occurring in the patient.

Preferably, a neurostimulator according to the invention is capable of detecting or predicting any kind of neurological event that has a representative electrographic signature. While the disclosed embodiment is described primarily as responsive to electrographic seizures characteristic of epilepsy, it should be recognized that it is also possible to respond to other types of neurological disorders, such as movement disorders (e.g. the tremors characterizing Parkinson's disease), migraine headaches, chronic pain, and neuropsychiatric disorders such as depression. Preferably, neurological events representing any or all of these afflictions can be detected when they are actually occurring, in an onset stage, or as a predictive precursor before clinical symptoms begin.

With continued reference to FIG. 1, the intracranially implanted neurostimulator 110 is affixed in the patient's cranium 112 by way of a ferrule 118. The ferrule 118 is a structural member adapted to fit into a cranial opening, attach to the cranium 112, and retain the neurostimulator 110. To implant the neurostimulator 110, a craniotomy is performed in the parietal bone anterior to the lambdoidal suture to define an opening 120 slightly larger than the neurostimulator 110. The ferrule 118 is inserted into the opening 120 and affixed to the cranium 112, ensuring a tight and secure fit. The neurostimulator 110 is then inserted into and affixed to the ferrule 118.

The neurostimulator 110 includes a lead connector 122 adapted to receive one or more electrical leads, such as a first deep brain stimulation lead 124 and a second cortical lead 126. The lead connector 122 acts to physically secure the leads 124, 126 to the neurostimulator 110, and facilitates electrical connection to conductors in the leads 124, 126 coupling one or more respective electrodes to circuitry within the neurostimulator 110. The lead connector 122 accomplishes this in a substantially fluid-tight environment with biocompatible materials.

The leads 124, 126 include a flexible elongated member having one or more conductors. As shown, the leads 124, 126 are coupled to the neurostimulator 110 via the lead connector 122. The proximal portion of the first lead 124 is generally situated on the outer surface of the cranium 112 (and under the patient's scalp), and extends between the neurostimulator 110 and a burr hole 114 or other cranial opening. The distal portion of the deep brain stimulation lead 124 enters the cranium 112 and is coupled to at least one depth electrode 130 implanted in a desired location in the patient's brain. The proximal portion of the second lead 126 is generally situated on the outer surface of the cranium 112 (and under the patient's scalp), and extends between the neurostimulator 110 and a burr hole (not visible) or other cranial opening. The distal portion of the cortical lead 126 enters the cranium 112 through the burr hole and is secured in place by a burr hole cover 132. The distal portion of the cortical lead 126 includes at least one cortical electrode (not visible) implanted in a desired location on the patient's brain.

The neurostimulator 110 includes a durable outer housing 128 fabricated from a biocompatible material, such as titanium. As the neurostimulator 110 is self-contained, the housing 128 encloses a battery and any electronic circuitry necessary or desirable to provide the functionality described herein, as well as any other features. A telemetry coil or other antenna may be provided outside of the housing 128 (and potentially integrated with the lead connector 122) to facilitate communication between the neurostimulator 110 and external devices.

Figure 2:
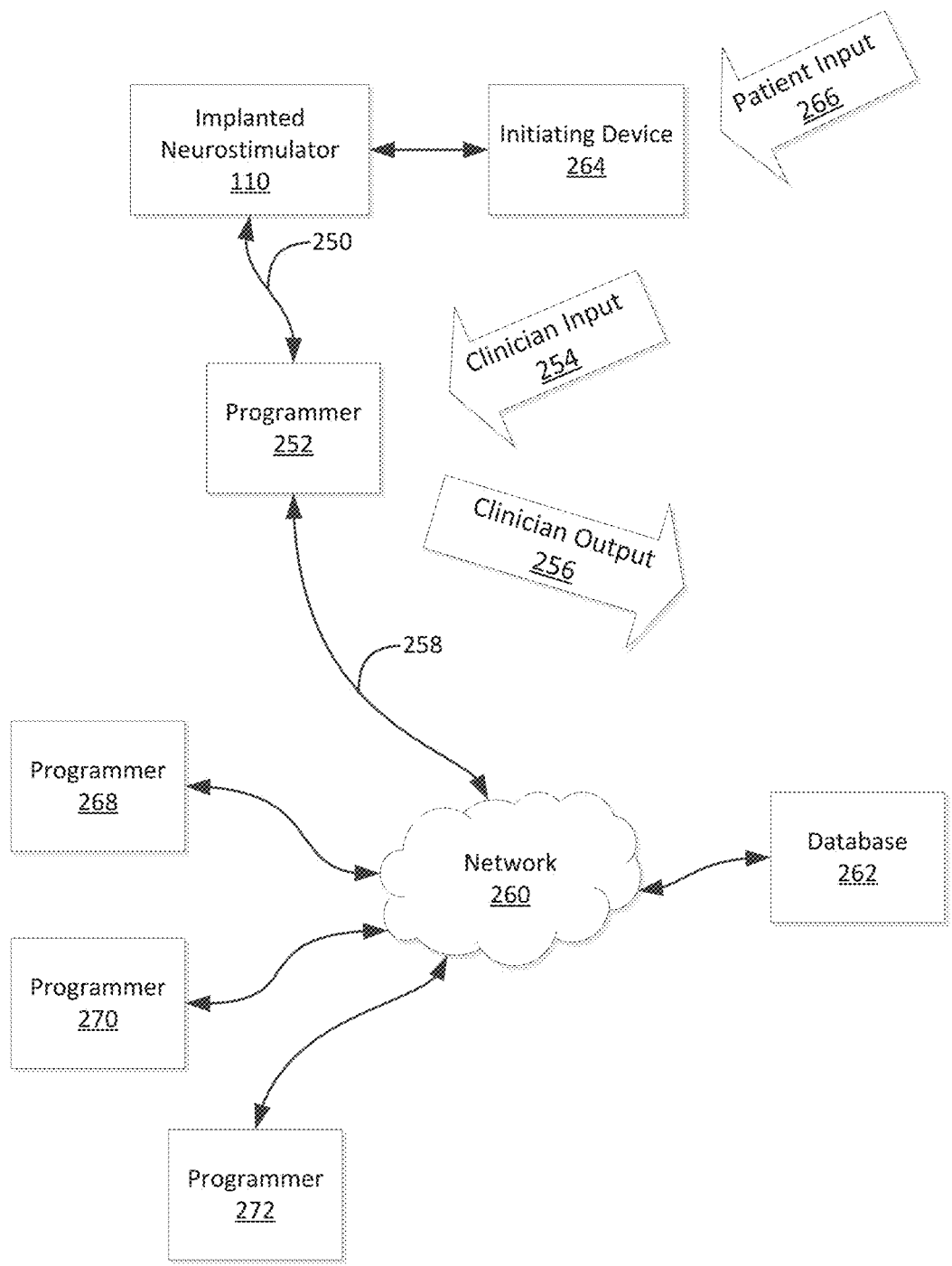
FIG. 2 is schematic of some of the implantable and external components of system according to embodiments, together with some of the inputs and outputs of the system.

FIG. 2 is an illustration of a responsive direct brain neurostimulation system showing one of the implantable components, several of the external components, and some of the possible system inputs and outputs. The neurostimulator 110 may include a selectable part-time wireless link 250 (e.g., short range or near field telemetry) to an external component such as a physician programmer 252. The wireless link 250 may be established using a USB peripheral connected to the programmer with a "wand" end that can be moved into communication range of the neurostimulator 110. The programmer 252 can then be used to manually control the operation of the neurostimulator, as well as to transmit information to or receive information from the neurostimulator 110.

The programmer 252 is capable of performing a number of advantageous operations. In particular, the programmer 252 is able to specify and set variable parameters in the neurostimulator 110. For example, the values of some parameters can be set to control the function of one or more tools that determine which features of a sensed electrographic signal the neurostimulator will detect as an "event" which triggers some response (e.g., generating and delivering a stimulation therapy) or other action (e.g., storing a record of the sensed electrographic signal at the time of detection and/or stimulation). The parameters that determine what the neurostimulator will detect as an event or events may be referred to as "detection parameters" or "detection sets". The parameters that determine what responsive stimulation will be generated may be referred to as "stimulation parameters" or "stimulation sets". Other parameters may be programmable to adapt the function of the neurostimulator to meet the patient's needs, upload or receive data from the neurostimulator 110 to the programmer 252, download or transmit program code and other information from the programmer 252 to the neurostimulator 110, or command the neurostimulator 110 to perform specific actions or change modes as desired by a physician operating the programmer 252. To facilitate these functions, the programmer 252 is adapted to receive clinician input 254 and provide clinician output 256; data is transmitted between the programmer 252 and the neurostimulator 110 over the wireless link 250.

The programmer 252 may be used at a location remote from the neurostimulator 110 if the wireless link 250 is enabled to transmit data over long distances. For example, the wireless link 250 may be established by a short-distance first link between the neurostimulator 110 and a transceiver, with the transceiver enabled to relay communications over long distances to a remote programmer 252 (e.g., long range telemetry), either wirelessly or via a wired communications link.

The programmer 252 may also be coupled via a communication link 258 to a network 260 such as the internet. This allows any information uploaded from the neurostimulator 110, as well as any program code or other information downloaded to the neurostimulator 110, to be stored in a database 262 at one or more data repository locations, which may include various servers and network-connected programmers like the programmer 252. This would allow a patient (and the patient's physician) to have access to important data, including past treatment information and software updates, essentially anywhere in the world that there is a programmer (like the programmer 252) and a network connection.

In some embodiments, the wireless link 250 from the neurostimulator 110 may enable a transfer of data from the neurostimulator to the database 262 without any involvement by the programmer 252. In these embodiments, the wireless link 250 may be established by a short-distance first link between the neurostimulator 110 and a transceiver, with the transceiver enabled to relay communications over long distances to the database 262, either wirelessly or via a wired communications link.

The neurostimulator 110 may be adapted to receive communications from an initiating device 224 (sometimes referred to as a "remote monitor"), typically controlled by the patient or a caregiver. Accordingly, patient input 266 from the initiating device 224 is transmitted over a wireless link to the neurostimulator 110. The patient input 266 may be used to cause the neurostimulator 110 to switch modes, e.g., turn between on to off, or perform an action, e.g., store a record of electrographic data. Preferably, the initiating device 224 is able to communicate with the neurostimulator 110, and possibly in the same manner the programmer 252 does. The link may be unidirectional, allowing commands to be passed in a single direction from the initiating device 224 to the neurostimulator 110. Alternatively, the link may be bi-directional, allowing status and data to be passed back from the neurostimulator to the initiating device 224. The initiating device 224 may be a computer configured as a laptop, a tablet, a smart phone or some other portable or mobile device.

In some embodiments, the programmer 252 is primarily a commercially available personal computer, such as in the form of a laptop, a tablet, or a workstation having a suitable central processing unit (CPU), user interface and accessories such as a keyboard, mouse and display, and running a standard operating system. The programmer also might be implemented as a turnkey system, with a custom software package so that the unit can be used only for functions dedicated to the neurostimulation system, for example, to minimize cybersecurity vulnerabilities.

The programmer 252 has the capability to allow a clinician to create or modify a patient-specific collection of information related to the detection of a neurological event, e.g., a seizure onset, and the treatment of the neurological event. The patient-specific information may include algorithms and associated algorithm parameters for the detection of relevant neurological events, and stimulation parameters for treatment.

The database 262 may be adapted to communicate over the network 260 with multiple programmers, including the programmer 252 and additional programmers 268, 270, and 272. Programmers may be located at various medical facilities and physician offices at widely distributed locations. Accordingly, if more than one programmer has been used to upload electrographic signals (also referred to as "electrocorticographic signals" or "electrocorticograms" or "ECoGs") from a patient's neurostimulator 110, the records or files may be aggregated via the database 262 and available thereafter to any of the programmers connected to the network 260, including the programmer 252.

In some embodiments, either the neurostimulator 110 or the programmer 252 can include a processor that can model seizures based on electrographic signals collected by the neurostimulator 110, sensed by electrodes of the neurostimulator 110. The seizures can be modeled to identify a canonical seizure termination for the seizures. The processor can create a stimulation therapy that emulates the canonical seizure termination, and the processor can provide the stimulation therapy to the neurostimulator 110.

Figure 3:
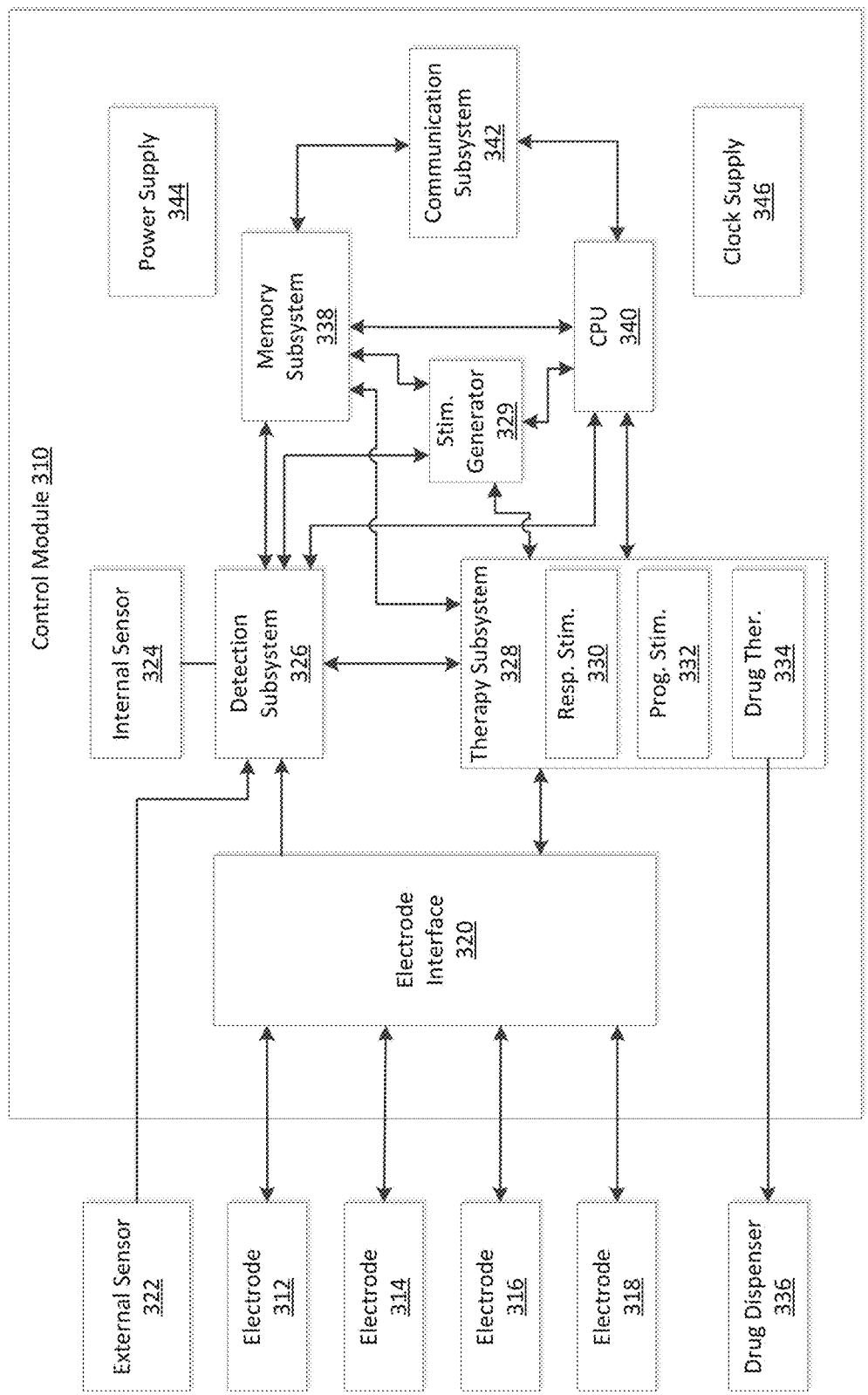
FIG. 3 is a block diagram of the implantable neurostimulator and electrode components of a system according to embodiments.

FIG. 3 is a block diagram of the neurostimulator 110 in which control module 310 includes several subsystems. The control module 310 is capable of being coupled to a plurality of electrodes 312, 314, 316, and 318, each of which may be connected to the control module 310 via a lead for sensing, stimulation, or a combination of the two functions. Thus, an electrode 312, 314, 316, 318 may be configured as either a sensor or a stimulator or both. The lead is coupled to the control module 310 through a lead connector (not shown in FIG. 3). Although four electrodes are shown, more electrodes may be available depending on the number of implanted leads and the number of electrodes per lead. For example, a pair of implanted leads, each with four electrodes, may be used to provide a total of eight electrodes.

The electrodes 312-318 are connected to an electrode interface 320. The electrode interface 320 is capable of selecting each electrode as required for sensing and stimulation. The electrode interface 320 may also provide any other features, capabilities, or aspects, including but not limited to amplification, isolation, and charge-balancing functions, that are required for a proper interface with neurological tissue. The electrode interface 320, an external sensor 322, and an internal sensor 324 are all coupled to a detection subsystem 326. The electrode interface 320 is also connected to a therapy subsystem 328.

In some embodiments, the control module 310 can determine an onset of a seizure from electrographic signals collected by the neurostimulator from the electrodes 312, 314, 316, and 318. The control module 310 can further select a stimulation therapy to generate and deliver when a seizure onset is detected. The stimulation therapy may comprise a burst or a plurality of biphasic pulses characterized by a burst duration, number of pulses, pulse width, and frequency. In some embodiments described herein, the stimulation therapy may comprise a pattern characterized by different or additional parameters, such as a parameter corresponding to an amplitude that is variable based on the characteristics of a canonical seizure termination which the stimulation therapy is intended to mimic. In some embodiments described herein, the stimulation therapy may be a fully-specified time series of current or voltage amplitudes mimicking the canonical seizure termination pattern itself, rather than an approximation that can be parameterized (see, e.g., FIGS. 16-18 and the corresponding description related to how stimulation therapies may be generated, including by relying on fixed and variable pulse attributes, etc.) In some embodiments, the stimulation therapy can be delivered via the electrodes 312, 314, 316, and 318. In some embodiments, the control module 310 can detect an instance of a seizure, and categorize the seizure into a type or group. In some embodiments, the type of seizure is determined based on features of the sensed electrographic signal and particularly on features identified at seizure onset or during seizure evolution. In some embodiments, selecting the stimulation therapy with which to respond to a detected seizure onset includes selecting a stimulation therapy that has been predetermined to correspond to the group the seizure belongs.

The detection subsystem 326 includes a data analyzer 414 with an EEG waveform analysis module 418. The EEG waveform analysis module 418 analyzes the electrographic signals sensed from the electrodes through the brain leads to decide whether the signals comprise any activity or represent any events which the neurostimulator is programmed to detect, for example, seizures.

The detection subsystem 326 may also include further sensing and detection functions, adapted to receive signals from the external sensor 322 or the internal sensor 324. These sensors 322, 324 may provide signals or other data elements representative of other physiological conditions, electrophysiological or not, such as temperature, blood pressure, etc.

For example, to detect a clinical seizure or patient orientation, it may be advantageous to provide an accelerometer, an angular velocity sensor, or an EMG sensing electrode as the external sensor at a location remote from the neurostimulator 110. Other sensors, such as for temperature, blood pressure, blood oxygenation, drug concentration, or neurotransmitter concentration, might be implemented as part of the external sensor 322 or the internal sensor 324. The external sensor 322 can be connected to the neurostimulator 110 by a lead or by wireless communication, such as a wireless intrabody signaling technique.

Such other sensors or probes may be either hard wired or in wireless communication with the neurostimulator 110 so that the neurostimulator may monitor physiological data other than data acquired using the electrodes. For example, probes for oximetry and micro/macroelectrode configurations for accomplishing voltammetric measurements relating to neurochemical concentrations may be used to provide other physiological data to the neurostimulator 110. A probe may be used to acquire a signal corresponding to the level of the near-infrared wavelength characteristic of light absorption by oxygenated hemoglobin (HbO2). This signal may be used to estimate a level of neural activity. For instance, the neurovascular coupling system causes vasodilation and increased cerebral perfusion in response to neural activity, such that, after an initial drop in oxygenated hemoglobin when the increased neural activity begins, the increased neural activity is then accompanied by an increase in oxygenated hemoglobin.

Variations of sensors or probes may be implemented using transducers for additional sensing modalities such as optical infrared spectroscopy. A given sensing modality may rely upon active electronics provided in the lead, especially at a distal portion of a lead close to where the physiological data is being sensed, to acquire physiological data for use by the neurostimulator 110. Alternatively, a given sensor may be associated locally with active electronics and the sensor information acquired may be communicated to the neurostimulator 110 wirelessly.

The therapy subsystem 328 is capable of applying electrical stimulation to neurological tissue through the electrodes 312-318. This can be accomplished in any of a number of ways. Preferably, therapeutic stimulation is provided in response to abnormal events such as seizures that are detected by the data analysis functions of the detection subsystem 326. Responsive stimulation is provided by a responsive stimulation function 330 of the therapy subsystem 328.

The therapy subsystem 328 and the data analysis functions of the detection subsystem 326 are in communication. This facilitates the therapy subsystem 328 to provide responsive stimulation as well as the detection subsystem 326 to block the amplifiers while stimulation is being performed to minimize stimulation artifacts.

The therapy subsystem 328 is also capable of a drug therapy function 334, in which a drug is dispensed from a drug dispenser 336, which may be integral with the control module 310 or an external unit. This capability can be provided either on a programmed basis or responsively, after an event is detected by the detection subsystem 326.

The control module 310 includes a memory subsystem 338 and a central processing unit (CPU) 340, which can take the form of a microcontroller. The memory subsystem 338 is coupled to the detection subsystem 326, and may receive and store data representative of sensed electrographic signals and other sensor data. The memory subsystem 338 is also coupled to the therapy subsystem 328 and the CPU 340. In addition to the memory subsystem 338, the CPU 340 is also connected to the detection subsystem 326 and the therapy subsystem 328 for direct control of those subsystems.

The stimulation generator 329 can automatically generate a stimulation therapy once selected. The stimulation therapy selected can be based on the output of a machine learning model which is configured to identify and then characterize the attributes of an individual's seizures, particularly, the individual's seizure terminations. The method includes training one or several machine learning models to identify seizure terminations from data collected from an individual or individuals, such as that data collected by a neurostimulator according to embodiments and stored in the database 262 of the system illustrated in FIG. 2. The method further includes identifying the seizure terminations when the one or several machine learning models are trained, generating one or several canonical seizure termination(s) from the identified seizure terminations, and generating a stimulation therapy from the one or several canonical seizure termination(s). As used herein, a "canonical seizure termination" is data representative of a group of seizure terminations, which seizure terminations can be represented in an electrographic signal. In some embodiments, the electrographic signal corresponds to time-series data. Each canonical seizure termination can be represented as an electrographic signal. In some embodiments, each group of seizure terminations can be identified in data collected from a single patient. The stimulation generator 329 is coupled to the detection subsystem 326, the memory subsystem 338, the therapy subsystem 328, and the CPU 340. The stimulation generator 329 can use data received from the detection subsystem 326 and/or the memory subsystem 338 to generate a stimulation therapy that approximates or mimics a canonical seizure termination based on data measured from the patient. Each canonical seizure termination and/or the stimulation therapy can be stored in the memory subsystem 338. The CPU 340 can, based on the stimulation therapy(ies) stored in the memory subsystem 338, direct the operation of the therapy subsystem 328 and/or provide the stimulation therapy selected for a given seizure onset to the therapy subsystem 328.

The control module 310 also includes a communication subsystem 342. The communication subsystem 342 enables communication between the neurostimulator 110 and the outside world, particularly the external programmer 252. The communication subsystem 342 may include a telemetry coil enabling transmission and reception of signals, to or from an external apparatus, via inductive coupling. Alternative embodiments of the communication subsystem 342 could use an antenna for an RF link or an audio transducer for an audio link. The control module 310 also includes a power supply 344 and a clock supply 346. The power supply 344 supplies the voltages and currents necessary for each of the other subsystems. The clock supply 346 supplies substantially all of the other subsystems with any clock and timing signals necessary for their operation.

It should be observed that while the memory subsystem 338 is illustrated in FIG. 3 as a separate functional subsystem, the other subsystems may also require various amounts of memory to perform the functions described above. Furthermore, while the control module 310 is preferably a single physical unit contained within a single physical enclosure, it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 340 and the other functional subsystems may also vary.

The neurostimulator 110 generally interacts with the programmer 252 as described below. Data stored in the memory subsystem 338 can be retrieved by the patient's physician through the wireless communication link 250, which operates through the communication subsystem 342 of the neurostimulator 110. A software operating program run by the programmer 252 allows the physician to read out a history of events detected including electrographic signal information recorded before, during, and after each event, as well as specific information relating to the detection of each event. The programmer 252 also allows the physician to specify or alter any programmable parameters of the neurostimulator 110. The software operating program also includes tools for the analysis and processing of recorded ECoG records to assist the physician in developing optimized detection parameters for each specific patient, and to identify which therapies are most advantageously associated with what event characteristics.

In some embodiments, the physician can use the programmer 252 to load one or several stimulation therapies, which can be generated based on one or several canonical seizure termination(s) and/or data gathered from the patient. In some embodiments, the programmer 252 can receive data gathered from the patient by the neurostimulator 110, generate one or several stimulation therapies based on this gathered data, and download the one or several stimulation therapies to the neurostimulator 110.

A neurostimulator 110 may be programmed by a physician to acquire physiological data from one or more sensing locations in a patient, and to process, analyze and evaluate the acquired physiological data in an effort to determine whether the acquired physiological data evidences what the neurostimulator 110 is programmed to recognize as a detected event. Physiological data may include electrographic data, such as electrographic signals, or non-electrographic data, such as pH data and neurochemical data. A detected event may include, for example, a seizure or a seizure onset.

With respect to electrographic signals, the neurostimulator 110 may be programmed with detection parameters (i.e., a detection parameter set) related to the operation of one or more analysis tools. These analysis tools are described further below and may include one or more of a half-wave tool, a line length tool, and an area tool. The neurostimulator 110 may process a segment of an acquired electrographic signal, e.g., an ECoG, using one or more of the analysis tools to determine if the segment satisfies an event detection criterion corresponding to one of the detection parameters. If the criterion is satisfied, an event is considered to be detected.

With respect to non-electrographic data, the neurostimulator 110 may be programmed to detect an event when a measure of such data is below or above a certain threshold level or trends too low, too high, or the like. Such measures may be, for example, a level or concentration of a neurotransmitter sensed by an external sensor 322 or internal sensor 324 of the neurostimulator 110.

The neurostimulator 110 may be further programmed to record data in the memory subsystem 338 related to the occurrences of the detected events. For example, the neurostimulator 110 may record the segment of the acquired electrographic signal for which a detection criterion was satisfied. The neurostimulator 110 may also record one or more time features related to the detected event, such as the time of the detected event, the time of the end of the detected event, and the duration of the detected event. Measures of non-electrographic data may also be recorded.

Patients may also provide an input to the device, for instance via swiping a magnet over the device, to indicate the occurrence of a clinical event, e.g., a clinical seizure. As noted above, the clinical symptoms that led to the conclusion that a patient is having a seizure may occur after or before an electrographic seizure onset or electrographic seizure. The running count of the number of clinical events may be stored in the memory subsystem 338. Then the number of clinical or electrographic seizures logged in the device over a particular period of time (e.g., 24 hours) may provide a measure of how effective the stimulation therapy is for the particular patient.

Figure 4:
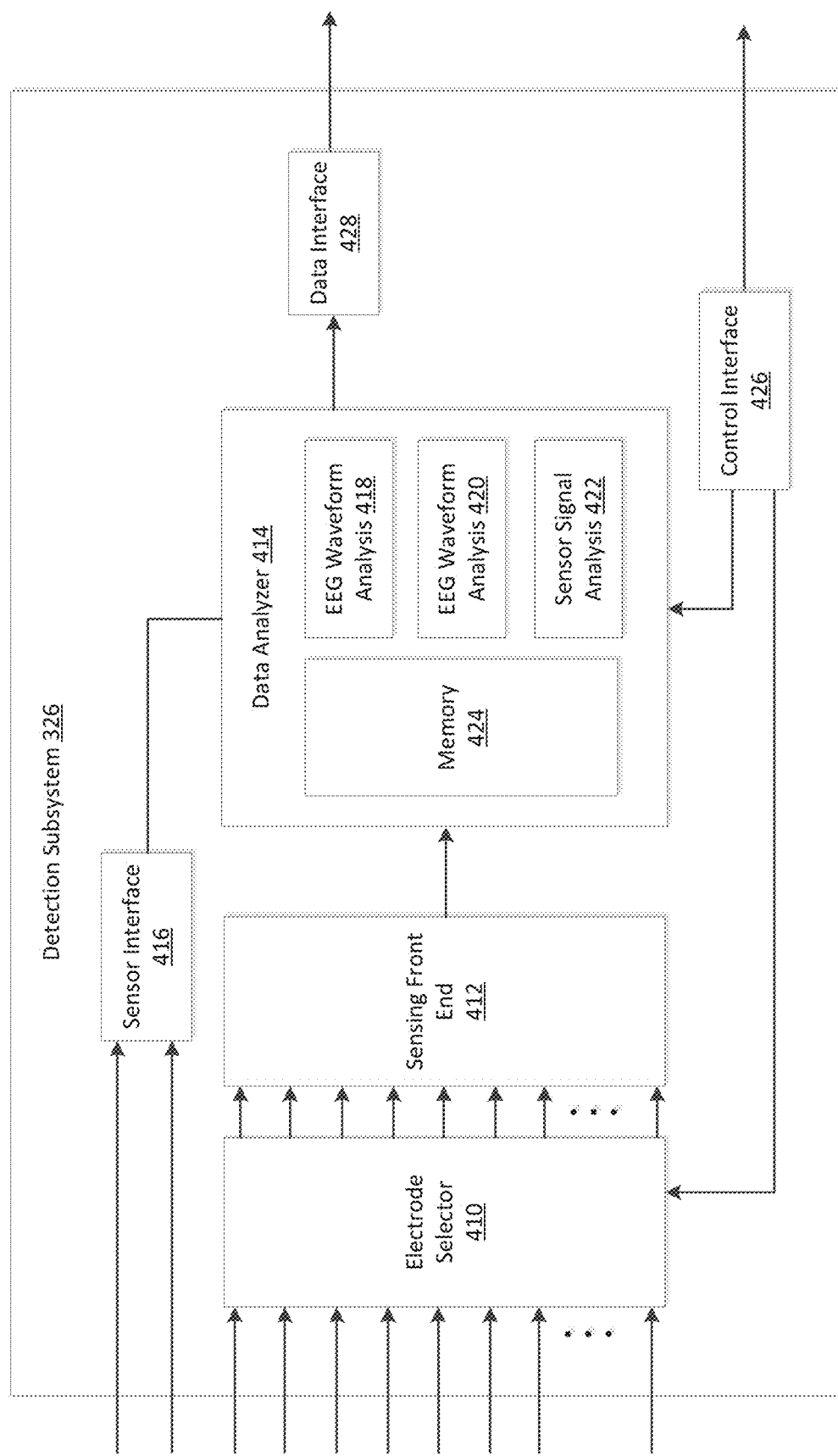
FIG. 4 is a block diagram of a detection subsystem of the control module of the implantable neurostimulator shown in FIG. 3.

FIG. 4 illustrates details of the detection subsystem 326. Inputs from the electrodes 312-318 are on the left and connections to other subsystems are on the right. Signals received from the electrodes 312-318 are received in an electrode selector 410. The electrode selector 410 allows the neurostimulator to select which electrodes 312-318 should be routed to which individual sensing channels of the detection subsystem 326, based on commands received through a control interface 426 from the memory subsystem 338 or the CPU 340. Preferably, each sensing channel of the detection subsystem 326 receives a bipolar signal representative of the difference in electrical potential between two selectable electrodes. The outer housing 128 of the neurostimulator 110 also can be used as an electrode in acquiring a measure of electrographic activity.

The electrode selector 410 provides signals corresponding to each pair of selected electrodes to a sensing front end 412, which performs amplification, analog to digital conversion, and multiplexing functions on the signals in the sensing channels. Preferably, any of the electrodes 312-318 can be unused (i.e., not connected to any sensing channel), coupled to a positive or negative input of a single sensing channel, coupled to the positive inputs of multiple sensing channels, or coupled to the negative inputs of multiple sensing channels.

A multiplexed input signal representative of all active sensing channels is fed from the sensing front end 412 to a data analyzer 414. The data analyzer 414 may be a special-purpose digital signal processor (DSP) adapted for use in some embodiments, or in some alternative embodiments, may comprise a programmable general-purpose DSP. The data analyzer 414 may be configured to perform three functions, namely, an EEG waveform analysis function 418, an electrophysiological waveform analysis function 420, and a sensor signal analysis function 422. It will be recognized that some or all of these functions can be performed with the same software or hardware in the data analyzer 414, by simply operating with different parameters on different types of input data. It is also possible to combine the three functions in many ways to detect neurological events or conditions, or to identify event characteristics. The data analyzer 414 may have its own scratchpad memory area 424 used for local storage of data and program variables when the signal processing is being performed.

The data analyzer 414 may be configured to analyze data it acquires corresponding to field potential measurements sensed using electrodes with one or all of three tools, known as the half-wave tool, the line-length tool, and the area tool. These tools are described in more detail below and, for example, the afore-cited U.S. Pat. No. 6,810,285 for; and U.S. Pat. No. 7,966,073 for "Differential Neurostimulation Therapy Driven By Physiological Therapy," issued Jun. 21, 2011, which is incorporated herein by reference in the entirety. The tools may be implemented in a combination of hardware and software, or entirely in one or the other, depending on overall system requirements such as power consumption limitations.

The half-wave tool, the line-length tool, and the area tool each may be characterized as a tool for analyzing electrographic signals. There may be multiple instances of each of these tools in the data analyzer 414, having detection parameters that can be programmed with different values of different instances of the tools selectable to operate on the data processed through different sensing channels. The results of the tools may be used alone or in combination to decide whether an event should be deemed to have been detected in the sample of the signal analyzed. Event in this context may refer to a neurological event associated with a neurological disorder. For example, in the case of epilepsy, an event may be one or both of an seizure or a seizure onset.

The half-wave tool measures characteristics of an ECoG signal related to the dominant frequency content of the signal. In general terms, a half wave is an interval between a local waveform minimum and a local waveform maximum. Each time a signal changes directions—from increasing to decreasing, or from decreasing to increasing—a new half wave is identified. The half-wave tool further identifies those half waves having a duration that exceeds a minimum duration criterion and an amplitude that exceeds a minimum amplitude criterion, as "qualified half waves." The number of qualified half waves within a limited time period is a quantity of interest, as it may be representative of neurological events manifested in the specified frequency range corresponding to the half wave criteria. The half wave tool, particularly when used on filtered ECoG data, can be used to identify the presence of signals in particular frequency ranges over certain periods of time, such as a frequency range that correlates well with a time when a patient is experiencing seizure activity. In an embodiment, for example, the analysis performed by the detection module includes detection of power within a frequency band, such as from 13 to 30 Hertz, by analyzing half-waves that occur in one or more time windows in a sampled electrographic signal sensed from the patient's brain and acquired by the neurostimulator 110.

The line length analysis tool is a simplification of waveform fractal dimension, allowing a consideration of how much variation an ECoG signal undergoes. Accordingly, the line length analysis tool enables the calculation of a "line length" for an ECoG signal within a time window. Specifically, the line length of a digital signal represents an accumulation of the sample-to-sample amplitude, variation in the ECoG signal within a time window. Stated another way, the line length is representative of the variability of the input signal. A constant input signal will have a line length approaching zero representative of substantially no variation in the signal amplitude, while an input signal that oscillates between extrema from sample to sample will approach the maximum line length. It should be noted that while "line length" has a mathematical-world analogue in measuring the vector distance travelled in a graph of the input signal, the concept of line length as treated herein disregards the horizontal (X) axis in such a situation. The horizontal axis herein is representative of time, which is not combinable in any meaningful way with information relating to the vertical (Y) axis, generally representative of amplitude.

The area analysis tool is a simplification of waveform energy. Accordingly, the area analysis tool in some embodiments enables the calculation of the area under the ECoG waveform curve within a time window. Specifically, the area function is calculated as an aggregation of the ECoG's signal total deviation from zero over the time window, whether positive or negative. The mathematical-world analogue for the area function is the mathematical integral of the absolute value of the ECoG function (as both positive and negative signals contribute to positive energy). Once again, the horizontal axis (time) makes no contribution to the area under the curve as treated herein. Accordingly, an input signal that remains around zero will have a small area, while an input signal that remains around the most-positive or most-negative values (or oscillates between those values) will have a high area.

Any of the three detection tools summarized above can be used in connection with any of the three functions of the data analyzer 414, and can be easily tuned to operate on essentially any kind of source data.

Different or additional tools may be used to evaluate ECoG waveforms, other electrophysiological waveforms and other sensor data. For example, an ECoG waveform may be analyzed in the frequency domain by a tool that involves fast Fourier transforms (FFTs). The analysis tools may be used alone or in combination (e.g., in a Boolean combination) to analyze the physiological data sensed from the patient. A tool or tools may be implemented entirely by the neurostimulator 110 or in part by the implant and in part by one or more external components. Physiological data acquired by the neurostimulator 110 may be subjected to more than one tool at the same time or to one tool followed by another tool.

The analyzing may include comparing a result of an algorithm or algorithms with one or more thresholds, fixed or dynamic, or other values. The results can be logically combined, thresholded, trended, or subjected to further analyses or processing steps as necessary to detect neurological events or states, to assess effectiveness of stimulation subspace, or to identify other characteristics in the acquired physiological data according to embodiments.

Any detection tool or other algorithm for analyzing data with the detection subsystem 326 easily may be tuned to operate on essentially any kind of source data. It will be apparent that detection of a pathological event can include the condition occurring when the output of one of these analysis tools exceeds or falls below a threshold, such as a programmable parameter representing the threshold between normal physiological variation and pathological neural activity. It also will be apparent that a pathological event may be deemed to have been "detected" when a combination of conditions occurs, such as a Boolean AND combination, Boolean OR combination, or other logical combination, or a time sequence of such conditions occurring such as the output of a first analysis tool exceeding a first threshold followed within one second by the output of a second analysis tool exceeding a second threshold.

In some embodiments, the detection subsystem 326 is configured to analyze the acquired physiological data by determining a quantity or a quality of periodic variation with which the acquired physiological data is characterized. This quantity or quality of periodic variation may comprise one or more of an ultradian, circadian, or circalunar variation. The quantity or quality of periodic variation may be identified as a characteristic of physiological data subjected to a line length tool (e.g., identified based on the variation of line length of an electrographic signal averaged over time or a count of pathological events). Determining the quantity or quality of the periodic variation may involve one or more of the following analytic approaches: (1) determining a frequency or period of the periodic variation; (2) determining a modulation depth of the periodic variation; (3) determining an autocorrelation of a physiological measurement (e.g., wherein successive values of the physiological measurement are correlated with each other and the degree of correlation is quantified in some manner relative to the successive values); (4) determining a correlation or a coherence between multiple physiological measurements; (5) determining a phase of a periodic variation with respect to a phase of a different physiological measurement; and (6) determining a phase of a periodic variation with respect to a time interval such as calendar days, 28-day intervals, a patient's sleep cycle, a patient's medication schedule, or a patient's menstrual cycle. The quantity or quality of periodic variation with which the acquired physiological data is characterized may be useful, for example, in assessing whether a stimulation parameter set is effective for a patient. For example, the effectiveness of a stimulation parameter set may be estimated to be inversely proportional to the autocorrelation of the count of events at a 28-day time difference.

Figure 5:
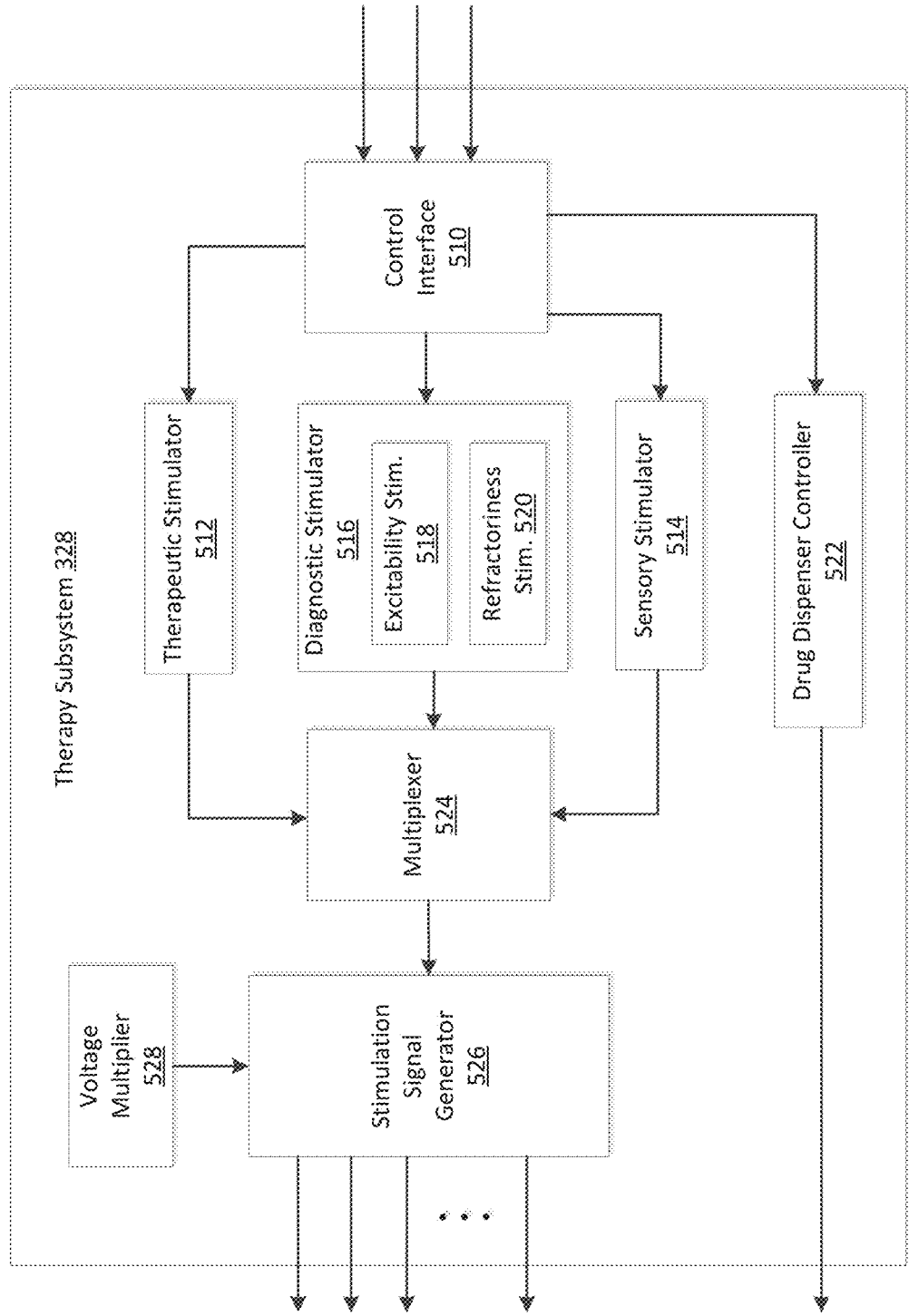
FIG. 5 is a block diagram of a therapy subsystem of the control module of the implantable neurostimulator shown in FIG. 3.

FIG. 5 is an illustration of the therapy subsystem 328. Inputs to the therapy subsystem 328 are shown on the right, and outputs are on the left. Referring initially to the input side, the therapy subsystem 328 includes a control interface 510, which receives commands, data, and other information from the CPU 340, the memory subsystem 338, and the detection subsystem 326. The control interface 510 uses the received commands, data, and other information to control a therapeutic stimulator 512, a sensory stimulator 514, and a diagnostic stimulator 516. The therapeutic stimulator 512 is adapted to provide electrical stimulation signals (e.g., a stimulation therapy) appropriate for application to neurological tissue to terminate a present or predicted undesired neurological event, especially a seizure or its precursor.

The therapeutic stimulator 512 is typically activated in response to conditions detected by the detection subsystem 326, but may also provide some substantially continuous or scheduled stimulation ("programmed stimulation"). The sensory stimulator 514 is also typically activated in response to detection of an event by the sensing subsystem. It may electrically stimulate enervated tissue, such as the scalp, to provide a tactile sensation to the patient, or may alternatively include an audio or visual transducer to provide audiovisual cues, such as warnings, to the patient.

Some embodiments of the neurostimulator 110 may include a diagnostic stimulator 516, which can be used to perform active electrophysiological diagnostic measurements. The diagnostic stimulator 516 may include an excitability stimulator 518 and a refractoriness stimulator 520, and may be implemented with the same or a different circuit under appropriate controls from the control interface 510. The excitability stimulator 518 and the refractoriness stimulator 520 both act under the control of the detection subsystem 326 to provide the stimulation signals used for the effective measurement of electrophysiological parameters in some embodiments. The excitability stimulator 518 may provide pulses at varying current levels to test the excitability of neural tissue, while the refractoriness stimulator 520 provides pairs of pulses with varying interpulse intervals to test the inhibitory characteristics of neural tissue.

The therapy subsystem 328 also may include a drug dispenser controller 522, which under the control of the control interface 510, is adapted to selectively allow the release of a drug or other therapeutic agent from a drug dispenser 336 to one or more desired sites, within or near the patient's brain or elsewhere in the body. As is the case with therapeutic stimulation, drug therapy can be performed in response to a detected neurological event or condition, on a substantially continuous basis or scheduled basis ("programmed drug therapy").

The therapeutic stimulator 512, the sensory stimulator 514, and the diagnostic stimulator 516 are all coupled to a multiplexer 524, which is controllable to select the appropriate types of therapy, for example, an instance of stimulation defined in accordance with a stimulation parameter set to be generated by the stimulation signal generator 526. The multiplexer 524 may allow only one type of therapy to be performed at a time, but in some embodiments, the multiplexer 524 allows different types of therapy, such as two instances of stimulation therapy defined in accordance with two different stimulation parameter sets, to be selectively applied to the different electrodes 312-318, either sequentially or substantially simultaneously. The stimulation signal generator 526 receives commands and data from the therapeutic stimulator 512, the sensory stimulator 514, and the diagnostic stimulator 516, and generates electrical stimulation signals having the desired characteristics that are properly time-correlated and associated with the correct electrodes, and receives power from a controllable voltage multiplier 528 to facilitate the application of a proper voltage and current to the desired neural tissue. The voltage multiplier 528 is capable of creating relatively high voltages from a battery power source, which typically has a very low voltage. The stimulation signal generator 526 has a plurality of outputs, which in the disclosed embodiment are coupled to the electrode interface 320. The stimulation signal generator 526 can perform signal isolation, multiplexing, and queuing functions if the electrode interface 320 does not perform such functions.

The neurostimulator 110 is configurable to store information in the memory subsystem 338. The information may relate to sensed physiological data (e.g., waveforms or filtered or processed waveforms), store information relating to one or more conditions of the neurostimulator 110 at the time the sensed information is acquired (e.g., a date/time stamp, whether an amplifier in a sensing channel of the neurostimulator is saturated and, if so, for how long, the stimulation etc.), or store information relating to the form of stimulation delivered to the patient, if any (e.g., information with which a delivered instance of stimulation may be identified or recognized, information corresponding to whether a desired amplitude of stimulation was achieved, etc.).

Information storing may be undertaken as part of one or more of a recording function or event counting or event logging function of the control module 310. For example, if the neurostimulator 110 is configured to identify as a neurological event a characteristic in the monitored electrographic activity it acquires (e.g., as a seizure onset neurological event type), then a function of the neurostimulator 110 may be to keep track of how many times it detects that neurological event over a fixed period of time (e.g., 24-hours) or a variable period of time (e.g., during a time when the patient is experiencing symptoms associated with the neurological disorder for which the patient is being treated). Another function of the neurostimulator 110 may be to store the sample of acquired physiological data in which each neurological event was detected (or digitized or otherwise processed), so that, for instance, a physician may later review the sample by interrogating the information stored on the implant. If the physiological data includes ECoGs sensed by measuring field potential changes at one or more sensing locations in the patient's brain, then what the neurostimulator 110 records may comprise ECoG records. The running count of the number of detected events may be stored in an event counting/logging module of the memory subsystem 338 and the ECoG may be recorded in a recording module of the memory subsystem 424.

Figure 6:
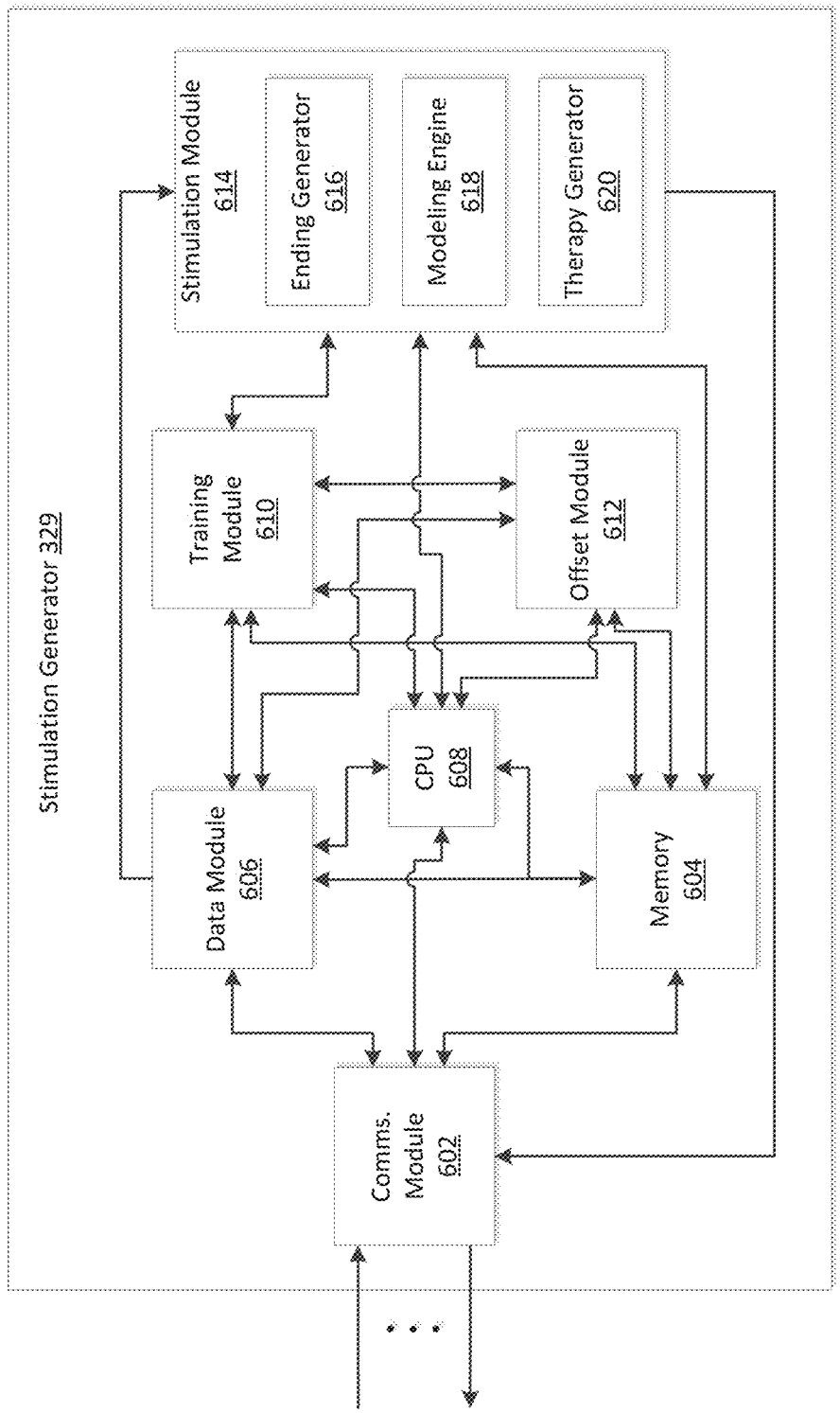
FIG. 6 is a block diagram of a stimulation generator of the control module of the implantable neurostimulator shown in FIG. 3.

FIG. 6 is an illustration of the stimulation generator 329 and/or of components of the programmer 252. In some embodiments, the neurostimulator 110 can automatically generate one or several stimulation therapies, as discussed above, and in some embodiments, the programmer can generate these one or several stimulation therapies with data downloaded from the neurostimulator 110, and the one or several stimulation therapies can then be downloaded to the neurostimulator 110 from the programmer 252. The programmer 252/stimulation generator 329 can include a communications module 602. The communications module can communicate with other components of the programmer 252/stimulation generator 329 via a wired or a wireless connection. In some embodiments, the communications module 602 can communicate with the wand to, for example, receive information at the programmer 252 from the neurostimulator 110.

The programmer 252/stimulation generator 329 can include a data module 606, a memory 604, and a central processing unit (CPU) 608, which can take the form of a microcontroller. The memory 604 can receive and store information received by the programmer 252/stimulator generator 329, and can be volatile or non-volatile memory. In some embodiments, the memory 604 can be a distinct physical component and in some embodiments, the memory 604 may be shared and/or partitioned with other processes and/or modules than shown in FIG. 6. In some embodiments, the memory 604 can be a partition within the memory of the neurostimulator 110 such as, for example, a partition within the memory subsystem 338.

The data module 606 can interact with the memory 604 to receive patient data characterizing one or several electrographic seizures. This patient data can be gathered from one or several patients. In embodiments in which the modules of FIG. 6 are located in the neurostimulator 110, the patient data can be gathered from the patient in which the neurostimulator 110 is implanted. In embodiments in which the modules of FIG. 6 are located in the programmer 252, the patient data can be gathered from one or more patients. The data module 606 can manage the patient data, and can, in some embodiments, divide the patient data into one or several sets of patient data such as, for example, a training set of patient data and a test set of patient data. The training set can be a set of time-series data characterizing a first plurality of seizures gathered from one or several patients. The test set can be a set of time-series data characterizing a plurality of seizures. The test set and the training set can, in some embodiments, be mutually exclusive. In some embodiments, the test set and the training set can be created from a set of time-series data characterizing a plurality of seizures from one or several patients. In some embodiments, the combination of the test set and the training set can include all of the time series data in the set of time-series data from which the test set and the training set are created, and in some embodiments, the combination of the test set and the training set can include less than all of the time-series data in the set of time-series data from which the test set and the training set are created. In some embodiments, multiple test and training sets can be created and can be used in the training of multiple machine learning models, in the validation of the multiple machine learning models, and in the selection of the best of the multiple machine learning models. After generation of the sets of patient data, the data module 606 can store the sets in the memory 604.

The programmer 252/stimulation generator 329 can include a training module 610, and offset module 612, and a stimulation module 614. The training module can train one or several machine learning models. These models can include a machine learning model trained to identify seizure terminations from time-series data gathered from one or several patients, a machine learning model trained to generate a canonical seizure termination from a plurality of provided seizure terminations, and/or a machine learning model to convert each canonical seizure termination into a stimulation therapy. In some embodiments, each canonical seizure termination can be data representing a set of time-series data from seizure terminations of one or several patients, and/or in some embodiments, the stimulation therapy can comprise instructions for directing operation of the neurostimulator to generate and deliver a stimulation therapy comprising one or several pulses. In embodiments in which the training module 610 trains one or several machine learning models with time-series data gathered from one or several patients, these machine learning models can then be used in generating one or several stimulation therapies custom to those one or several patients. The training of the machine learning models can be supervised and/or unsupervised. The training module 610 can be coupled to the memory 604 and can store trained machine learning models in the memory.

The offset module 612 can identify seizure terminations in time-series data gathered from one or several patients using the model trained to identify the seizure terminations by the training module 610. In some embodiments, this can include the inputting time-series data into the trained machine learning model. In some embodiments, for example, the offset module 612 can receive a machine learning model from the training module 610 and/or from the memory 604. The offset module 612 can further receive a set of time-series data for ingestion into the machine learning model from the data module 606 and/or from the memory 604. This set of time-series data can be ingested into the machine learning model, which machine learning model can output identified seizure terminations, which seizure terminations can be stored in the memory and/or provided to the stimulation module 614.

The stimulation module 614 can, based on one or several identified seizure terminations, generate a stimulation therapy. This can include generation of one or several canonical seizure terminations with the ending generator 616, the determining of a waveform shape that characterizes each canonical seizure termination with the modeling engine 618, and the generation of a stimulation therapy based on the waveform shape with the therapy generator 620. In some embodiments, the one or several canonical seizure terminations can be generated from the identified seizure terminations. In some embodiments, determining the waveform shape to characterize the canonical seizure termination can include applying the electrographic signal representing the canonical seizure termination to the modeling engine 618, which modeling engine can be an analyzer. The stimulation module 614 can output a stimulation therapy, which can be stored in the memory 604 and can be used by the neurostimulator 110 to generate and deliver a stimulation therapy comprising one or several pulses to the patient when an electrographic seizure is detected and/or when a different, previous electrical stimulation intervention fails to terminate a seizure.

Figure 7:
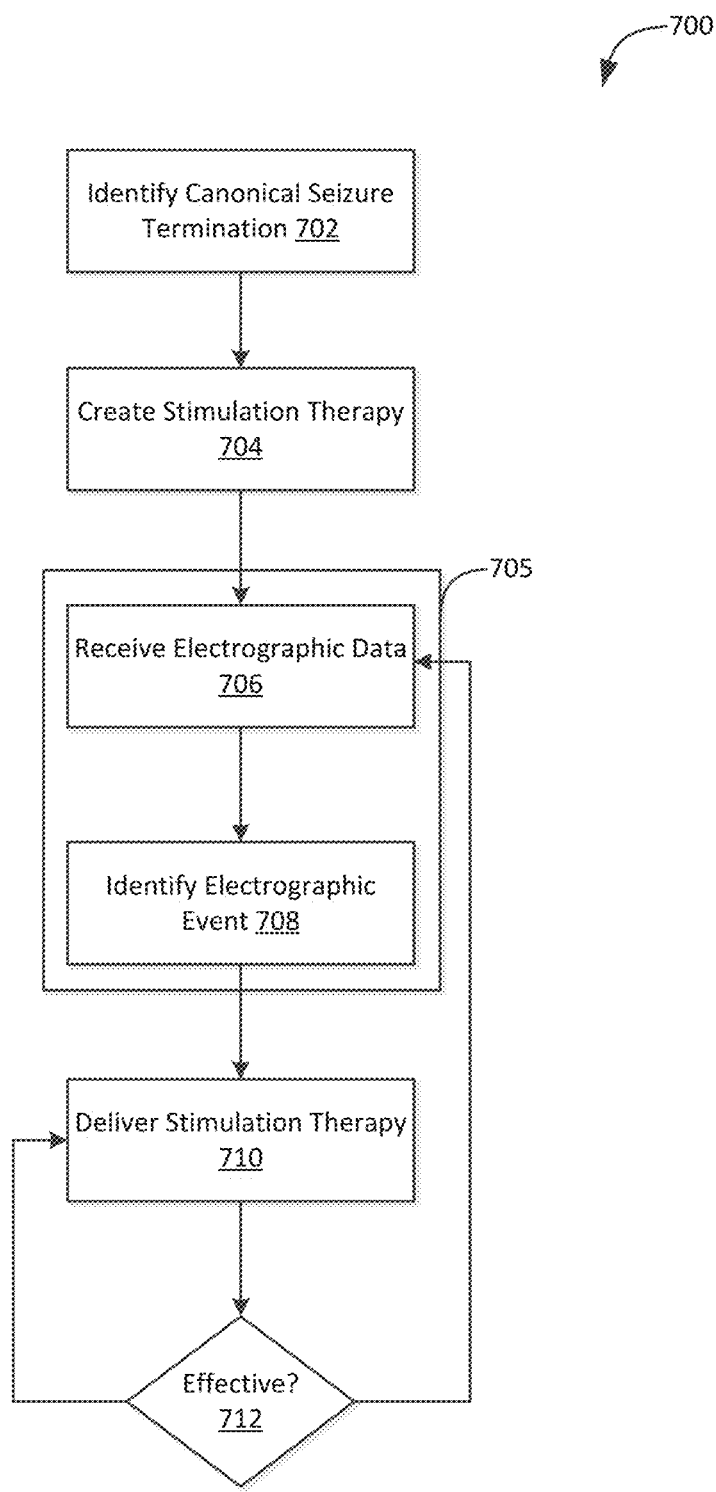
FIG. 7 is a flowchart illustrating a process according to embodiments for treating a patient's electrographic seizures with electrical stimulation.

FIG. 7 is a flowchart illustrating one embodiment of a process 700 for treating a patient's electrographic seizures with electrical stimulation. The process can be performed by the neurostimulator 110 and the programmer 252. The process 700 begins at block 702, wherein a canonical seizure termination is identified. In some embodiments, this can include modeling a plurality of seizures to identify the canonical seizure termination that corresponds to that plurality of seizures. In some embodiments, this can include receiving time-series data characterizing a plurality of seizures for one or several patients. The canonical seizure termination can be identified based on seizure terminations in this data. In some embodiments, the canonical seizure terminations can be determined via one or both of: dynamic time warping followed by averaging (or using the median or mode) across the seizure terminations; or use of a machine learning model trained to generate a canonical seizure termination based on ingested seizure termination data. In some embodiments, for example, the canonical seizure termination corresponds to time-series data derived by averaging the seizures after time-aligning the seizures using dynamic time warping. Additional disclosure of embodiments for identifying canonical seizure terminations are provided below with reference to FIGS. 8, 11, and 13.

In some embodiments, modeling the plurality of seizures can include training a machine learning model with time-series data corresponding to a plurality of electrographic seizures obtained from one or several patients. In some embodiments, the machine learning model can be trained to identify seizure terminations within the time-series data corresponding to the plurality of seizures obtained from the one or several patients, and/or to generate the canonical seizure termination. In some embodiments, this machine learning model can comprise at least one of: a clustering algorithm; a classifier; a shallow neural network model; a deep neural network model; a hidden Markov model; or a recurrent neural network model; or any combination thereof, such as, for example, a long short-term memory (LSTM) neural network. Additional disclosure of embodiments for identifying canonical seizure terminations are provided below with reference to FIGS. 8, 11, 14, and 15.

In block 704 of the process 700, a stimulation therapy is created. This stimulation therapy can emulate all or portions of the canonical seizure termination such that an electrical stimulation intervention comprising the stimulation therapy at least partially emulates or mimics electrographic activity naturally occurring at the patient's seizure terminations. The stimulation therapy can be generated by the stimulation module 614.

In some embodiments, the generation of the stimulation therapy can include creating pulse characterization data based on the canonical seizure termination. This pulse characterization data can identify one or several pulses forming the stimulation therapy, and one or several attributes of these one or several pulses. In some embodiments, these one or several attributes can include, for example, a pulse timing within the stimulation therapy, a pulse frequency, a pulse amplitude, and/or a pulse duration. In some embodiments, the pulse characterization data can be translated by the therapy subsystem 328 into one or several pulses that can be delivered to the patient. Additional disclosure of embodiments on creating stimulation therapy are provided below with reference to FIGS. 8, 10, 11, and 12.

At block 705, a patient's electrographic activity is monitored for instances of electrographic seizure. This monitoring can be performed by the neurostimulator and can include the steps of block 706 and 708. At block 706, electrographic signals for a patient is received. In some embodiments, the electrographic data can be received by the neurostimulator 110 via one or several leads 222 of the neurostimulator 110. This electrographic data can comprise time-series data characterizing electrographic events in the patient's brain. In some embodiments, this electrographic data can be received as a stream of data as it is being collected by one or several leads 222. In some embodiments, and as depicted in block 708, the received electrographic data can be evaluated and an electrographic seizure can be identified based on the received electrographic data. In some embodiments, the detection subsystem 326 can identify electrographic seizures from the received electrographic data based on one or several characteristics and/or features of the received electrographic data. In some embodiments, the detection subsystem 326 can identify electrographic seizures based on detection of one or several onsets of the electrographic seizures.

At block 710, the neurostimulator 110 can respond to detection of an electrographic seizure via delivery of a stimulation therapy comprising one or several pulses. In some embodiments, this stimulation therapy can be delivered in response to the detection of a seizure onset. In some embodiments, this can include providing the stimulation therapy from the stimulation generator 329 to the therapy subsystem 328, which therapy subsystem can, in some embodiments, translate the pulse characterization data into a train of stimulation pulses delivered to the patient. In some embodiments, the therapy subsystem 328 can generate and deliver one or several electrical pulses to the patient, and specifically to portions of the patient's brain via one or several of electrodes 312, 314, 316, 318.

After stimulation has been delivered, the process 700 proceeds to decision state 712 wherein it is determined if the stimulation was effective. In some embodiments, this can include receiving and evaluating electrographic data to determine whether the seizure ended. Whether the stimulation therapy was effective can be assessed by, for example, the detection subsystem 326. In some embodiments, if it is determined that stimulation is not effective, then the process 700 returns to block 710 wherein further stimulation is delivered, and the process 700 can proceed until the electrographic seizure has terminated and/or until some termination criterion is met. In some embodiments, this criterion may relate to the amount of stimulation provided to a patient, and specifically, the process 700 may terminate when a predetermined amount of stimulation is delivered without terminating the electrographic seizure. Alternatively, if it is determined that the stimulation is effective in that the electrographic seizure has terminated, then the process 700 can return to block 706 and proceed as outlined above.

Figure 8:
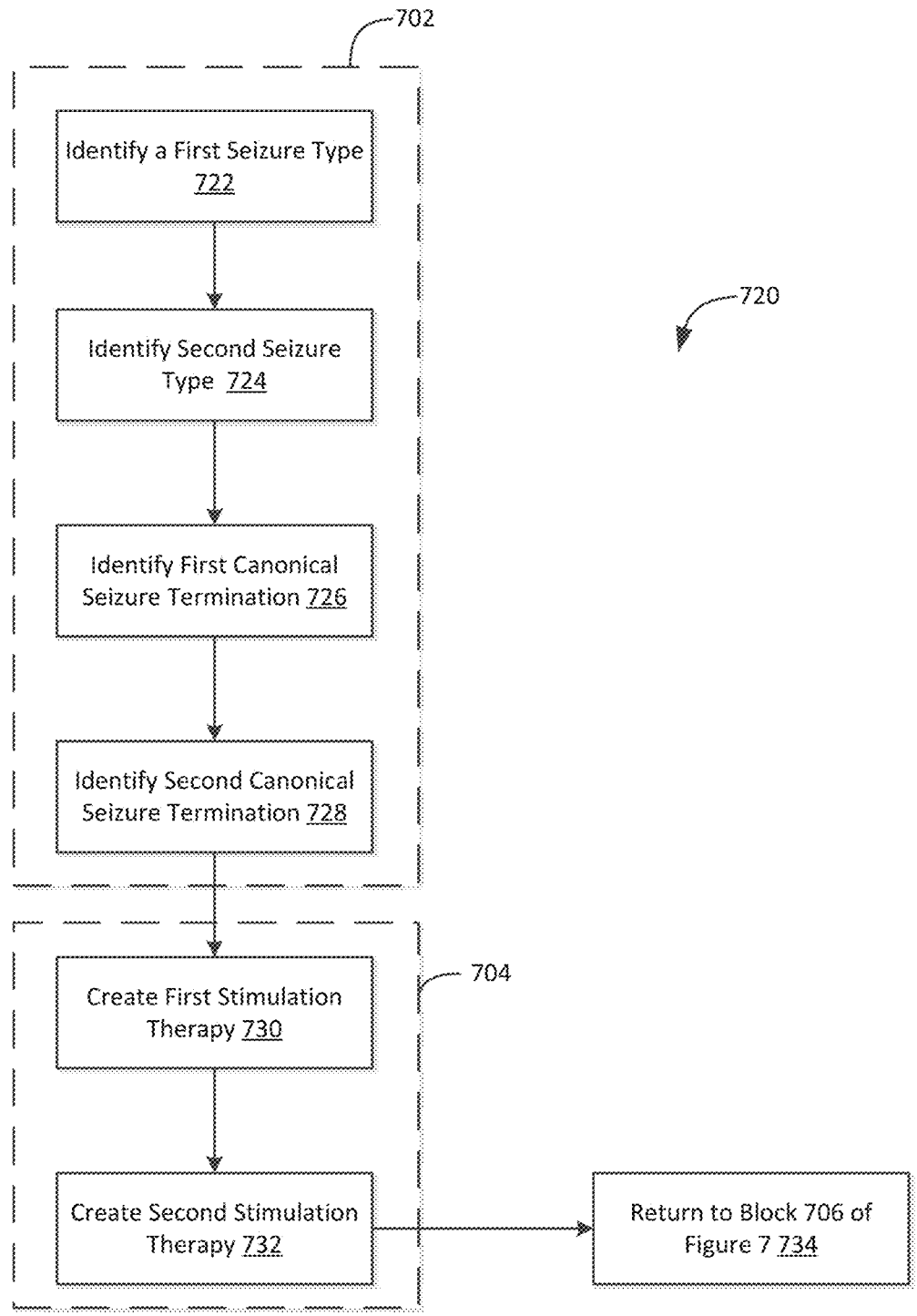
FIG. 8 is a flowchart illustrating a process according to embodiments for identifying a canonical seizure termination and for generating a stimulation therapy.

With reference now to FIG. 8, a flowchart illustrating one embodiment of a process 720 is shown. The process 720 can include a first set of steps comprising some or all of blocks 722 through 728, that can be performed as a part of or in the place of block 702 of FIG. 7, and a second set of steps comprising some or all of block 730 and 732, that can be performed as a part of or in the place of block 704 of FIG. 7.

The process 720 begins at block 722 wherein a first seizure type is identified in the received electrographic data for the patient. In some embodiments, one or several types of electrographic seizures can be identified in the electrographic data for the patient. In some embodiments, these electrographic seizure types can be identified based on commonalities between electrographic seizures. For example, a first type of electrographic seizures may be associated with a first set of characteristics or features identifiable in the patient's electrographic data and a second type of electrographic seizures may be associated with a second set of characteristics or features identifiable in the patient's electrographic data. In some embodiments, these features used to distinguish types of seizures can be identified via one or several machine learning techniques and specifically via one or several unsupervised machine learning techniques.

In some embodiments, for example, features of electrographic data can be used to distinguish types of seizures via the use of one or several machine learning techniques such as, for example, clustering, neural networks, or the like. In one embodiment, for example, a deep learning model is applied to electrographic data to extract features from that data and provide a multi-dimensional feature vector. The features extracted from the electrographic data by the deep learning model are believed to include hierarchically filtered versions of the data forming the record. The deep learning model may be, for example, a pretrained convolution neural network, an autoencoder, a generative model, a recurrent neural network containing a deep learning architecture, such as, for example, a long short-term memory network, or a deep neural network configured to derive features from the electrographic data.

These types of deep learning models are described, for example, in: Deep Learning, by Yann LeCun et al., Nature, May 27, 2015, Volume 521, pp 436-444; Epileptic Seizure Detection: A Deep Learning Approach, by Ramy Hussein et al., ArXiv:1803.09848v1, Mar. 27, 2018, pp 1-12; 2018; A Long Short-Term Memory deep learning network for the prediction of epileptic seizures using EEG signals, by Kostas M. Tsiouris et al., Computers in Biology and Medicine, Volume 99, Aug. 1, 2018, pp 24-37; Learning Robust Features using Deep Learning for Automatic Seizure Detection, by Pierre Thodoro et al., ArXiv:1608.00220, Jul. 31, 2016, pp 1-12; Autoencoders for learning template spectrograms in electrocorticographic signals, by Tejaswy Pailla et al., Journal of Neural Engineering, Volume 16, Number 1, Jan. 14, 2019; Waveform Modeling and Generation Using Hierarchical Recurrent Neural Networks for Speech Bandwidth Extension, Zhen-Hua Ling et al., IEEE/ACM Transactions on Audio, Speech, and Language Processing, Volume 26, Number 5, pp. 883-894, May 2018; and Visualizing and Understanding Convolutional Networks, by Matthew D. Zeiler et al., ArXiv:1311.2901v3, Nov. 28, 2013, pp 1-11, each of which is herein incorporated by reference.

Feature extraction may also be done through pretrained deep learning models, such as AlexNet or Inception-v3; or by training the deep learning models from scratch. AlexNet is described in ImageNet Classification with Deep Convolutional Neural Networks, by A. Krizhevsky, I. Sutskever, and G. Hinton, included in Advances in Neural Information Processing Systems 25 (NIPS 2012), available at http://papers.nips.cc/paper/4824-imagenet-classification-with-deep-convolutional-neural-networks, which is herein incorporated by reference. Other types of feature extraction techniques may be used to extract features. For example, handcrafted algorithms, such as spectral power algorithms, Fast Fourier Transform algorithms or wavelet features algorithms, may be used to extract features.

A clustering algorithm, such as k-means clustering, may then be applied to the feature vectors provided by the deep learning model to identify one or several clusters of electrographic seizures. Each of these clusters of seizures can represent a type of electrographic seizure. And in some embodiments, identifying a first seizure type can include generating multiple clusters from electrographic seizure data for patient, and associating one of the clusters with a first seizure type. The first electrographic seizure type can be identified with, for example, the offset module 612. K-means clustering is a method of vector quantization, originally from signal processing, that is popular for cluster analysis in data mining. K-means clustering aims to partition n observations into k clusters in which each observation belongs to the cluster with the nearest mean, serving as a prototype of the cluster. This results in a partitioning of the data space into Voronoi cells. The problem is computationally difficult (NP-hard); however, efficient heuristic algorithms converge quickly to a local optimum. These are usually similar to the expectation-maximization algorithm for mixtures of Gaussian distributions via an iterative refinement approach employed by both k-means and Gaussian mixture modeling. They both use cluster centers to model the data; however, k-means clustering tends to find clusters of comparable spatial extent, while the expectation-maximization mechanism allows clusters to have different shapes. Alternatively, the Bayesian Gaussian Mixture Models may be used for clustering. This method of clustering has the advantage of implicitly deriving the number of clusters. Several clustering algorithms are described in Survey of Clustering Algorithm, by Rui Xu and Donald C. Wunsch, IEEE Transactions on Neural Networks, Institute of Electrical and Electronics Engineers, May 2005, which is herein incorporated by reference.

At block 724, a second seizure type is identified. In some embodiments, the second seizure type can be identified from the electrographic seizure data for the patient. In some embodiments, the second seizure type can be identified in the same way as the first seizure type is identified, and in some embodiments in which clusters are generated from the patient's electrographic seizure data, the identifying of the second type can include associating a second one of the clusters with the second seizure type. The second electrographic seizure type can be identified with, for example, the offset module 612.

In some embodiments, the steps of blocks 722 and 724 together comprise dividing the electrographic data for the electrographic seizures into at least a first group comprising the first electrographic seizure type and a second group comprising the second electrographic seizure type. In some embodiments, as the electrographic data for the electrographic seizures can include electrographic data for the seizure terminations, the dividing of the electrographic data for the electrographic seizures into at least the first group and the second group can include dividing the seizure terminations into at least the first group and the second group. In some embodiments, the electrographic seizures can be divided into the groups based on one or several attributes associated with the electrographic seizures and captured in the electrographic data associated with the electrographic seizures. In some embodiments, these attributes can be attributes of the electrographic seizures that precede the seizure termination, and thus occur in the onset or during evolution or development.

At block 726, a plurality of first seizures corresponding to the first seizure type are modeled to identify a first canonical seizure termination. In some embodiments, this can include identifying the seizures associated with the first seizure type, and generating the canonical seizure termination for these identified seizures associated with the first seizure type. As disclosed in general above and in detail below with reference to FIGS. 13, 14 and 15, this canonical seizure termination can be generated via, for example, one or several of: dynamic time warping followed by averaging; or use of a machine learning model trained to generate a canonical seizure termination based on ingested seizure termination data.

At block 728, a plurality of second seizures corresponding to the second seizure type are modeled to identify a second canonical seizure termination. In some embodiments, this can include identifying one or several seizures associated with the second seizure type, and generating the canonical seizure termination for these identified seizures associated with the second seizure type. As disclosed in general above and in detail below with reference to FIGS. 13, 14 and 15, this canonical seizure termination can be generated via, for example, one or several of: averaging; dynamic time warping; or use of a machine learning model trained to generate a canonical seizure termination based on ingested seizure termination data.

At block 730, a first stimulation therapy is created and/or generated. In some embodiments, the first stimulation therapy can be created and/or generated to emulate all or portions of the first canonical seizure termination. In some embodiments, this can include the generation of a stimulation therapy having one or several frequencies common with the first canonical seizure termination and/or extracted from the first canonical seizure termination. In some embodiments, the generation of the first stimulation therapy can include the generation of one or several pulses for delivery to the patient, which one or several pulses share(s) attributes with the first canonical seizure termination. These shared attributes can include, for example, pulse frequency, pulse amplitude, or pulse width. In some embodiments, the first stimulation therapy can be associated with the first seizure type, and can be stored in the memory 604. Additional disclosure of embodiments on creating stimulation therapy are provided below with reference to FIGS. 10, 11, and 12.

In block 732, a second stimulation therapy is created and/or generated. In some embodiments, the second stimulation therapy can be created and/or generated to emulate all or portions of the second canonical seizure termination. In some embodiments, this can include the generation of a stimulation therapy having one or several frequencies common with the second canonical seizure termination, and/or extracted from the second canonical seizure termination. In some embodiments, the generation the second stimulation therapy can include the generation of one or several pulses for delivery to the patient, which one or several pulses share attributes with the second canonical seizure termination. These shared attributes can include, for example, pulse frequency, pulse amplitude, or pulse width. In some embodiments, the second stimulation therapy can be associated with the second seizure type, and can be stored in a memory 604. Additional disclosure of embodiments on creating stimulation therapy are provided below with reference to FIGS. 10, 11, and 12.

After the creation and/or generation of the second stimulation therapy, the process 700 can proceed to block 734, and can return to block 706 of FIG. 7. As will readily be appreciated by one skilled in the art, an individual's seizures may be characterized into more than two different seizure types, and a different canonical seizure termination can be developed for each of how many different seizure types there may be, and consequently a stimulation therapy can be generated for however many different canonical seizure terminations there may be.

Figure 9:
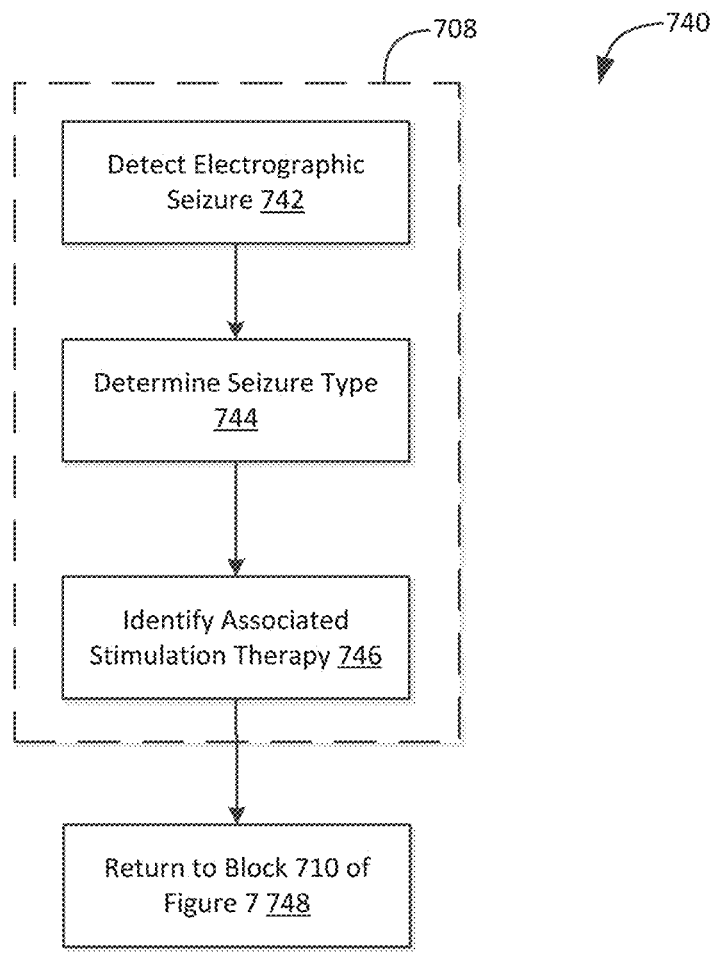
FIG. 9 is a flowchart illustrating a process according to embodiments for identifying a seizure onset, a seizure type, and a stimulation therapy for the seizure onset and the seizure type.

With reference now to FIG. 9, a flowchart illustrating one embodiment of a process 740 for identifying an electrographic event is shown. The process can be performed as a part of, or in the place of block 708 of the process 700 of FIG. 7. The process 740 begins a block 742 wherein an electrographic seizure and/or an instance of an electrographic seizure is detected. In some embodiments, this detection can be performed by the detection subsystem 326. As noted above, a seizure may be identified as described in U.S. Pat. No. 6,810,285, filed on Jun. 28, 2001, and entitled "Seizure Sensing and Detection Using an Implantable Device."

After the electrographic seizure has been detected, the process 740 proceeds to block 744 wherein a seizure type is determined for the detected electrographic seizure. In some embodiments, this can include extracting one or several features or attributes from the electrographic data associated with the detected electrographic seizure. In some embodiments, these one or several features or attributes can be extracted from electrographic data in the onset and/or during seizure evolution or development. These one or several features or attributes can be indicative of one or several characteristics of the seizure associated with the data from which the one or several features or attributes are extracted. These one or several features or attributes can be used to determine the seizure type of the associated seizure, and specifically, these one or several features or attributes can be compared to features or attributes characteristic of the identified seizure types. Based on this comparison, the type of seizure for the detected seizure can be determined. In some embodiments, the detection subsystem 326 can determine the type of seizure for the detected seizure. As noted above, a type of seizure may be identified as described in U.S. Publication No. 2016/0228705, filed on Feb. 10, 2016, and entitled "Seizure Onset Classification and Stimulation Pattern Selection."

After the seizure type has been determined for the detected seizure, the process 740 proceeds to block 746 wherein the stimulation therapy associated with the determined seizure type is identified. In some embodiments, this can include querying the memory 604 for the stimulation therapy associated with the determined seizure type. In response to the query, the memory 604 can identify the stimulation therapy associated with the determined seizure type, and can provide the stimulation therapy. In some embodiments, for example, the memory 604 can provide the stimulation therapy to the therapy subsystem 328. After the stimulation therapy associated with the seizure type has been identified, the process 740 proceeds to block 748, and returns to block 710 of FIG. 7, wherein the stimulation therapy is generated and delivered according block 746.

Figure 10:
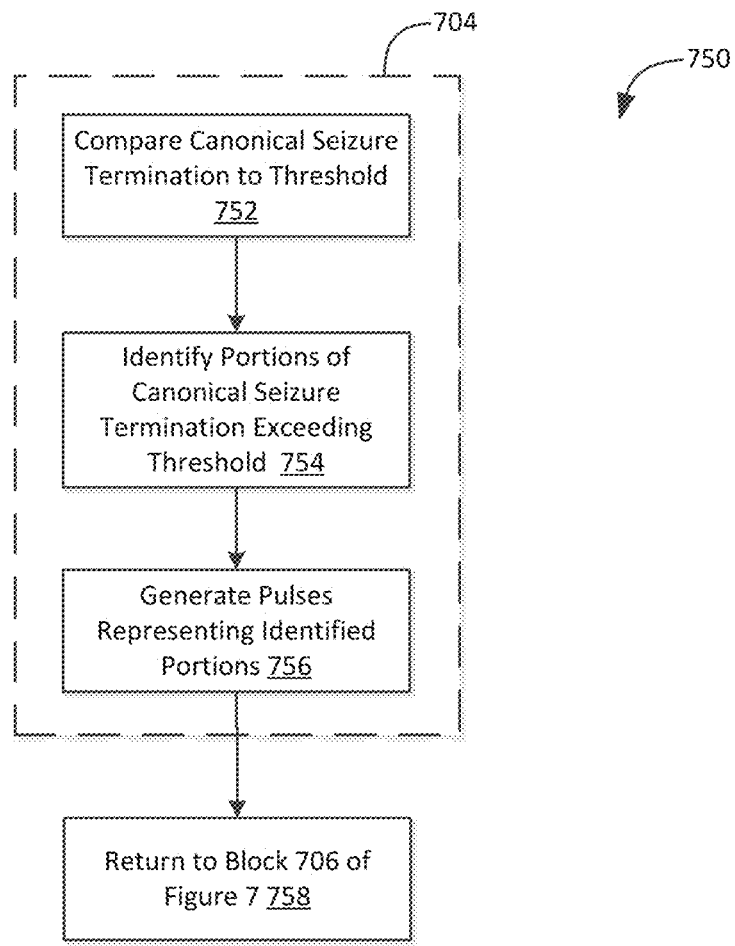
FIG. 10 is a flowchart illustrating a process according to embodiments for creating a stimulation therapy based on a canonical seizure termination.

With reference now to FIG. 10, a flowchart illustrating one embodiment of a process 750 for creating a stimulation therapy is shown. The process 750 can be performed as a part of, or in the place of block 704, of FIG. 7. The process 750 begins at block 752, wherein the canonical seizure termination is compared to a threshold. In some embodiments, this can serve to filter out portions of the canonical seizure termination that are below the threshold, and more specifically to filter out portions of the canonical seizure termination that have an amplitude less than a threshold value. In some embodiments, comparing the canonical seizure termination to the threshold enables discretizing of the canonical seizure termination into a train of stimulation pulses, e.g., discretizations, retrieving the threshold value from, for example, the memory 604, and comparing some or all of the values of the amplitude at each timepoint of the canonical seizure termination to the threshold. In some embodiments, an amplitude having a value exceeding the threshold is associated with an indicator of this status, and/or an amplitude having a value not exceeding the threshold is associated with an indicator of this status. The comparison of the canonical seizure termination to the threshold can be performed by the therapy generator 620. In one example, discretizations having a value above a certain voltage threshold are set to 1, and all values below that threshold to 0 (i.e. turning continuous voltage values into one of two possible discrete values). Each continuous period whose discretizations are set to 1 specify the time and duration of a stimulation pulse. This is one way to derive a train of stimulation pulses from a continuous waveform (e.g. to obtain a set of stimulation pulse times and durations from a canonical seizure ending).

After comparing the canonical seizure termination to the threshold, the process 750 can proceed to block 754, wherein portions of the canonical seizure termination exceeding the threshold are identified. In some embodiments, the identification of the portions of the canonical seizure termination exceeding the threshold can include a quantifying of the degree to which the portions of the canonical seizure termination exceed the threshold. In some embodiments, this quantifying can include: selecting a portion of the canonical seizure termination exceeding the threshold and/or of the waveform shape characterizing the canonical seizure termination exceeding the threshold; comparing the selected portion of the canonical seizure termination and/or of the waveform shape to the threshold; and determining a difference between the threshold and the selected portion of the canonical seizure termination and/or of the waveform shape of the threshold. The identifying of portions of the canonical seizure termination exceeding the threshold can be performed by the therapy generator 620.

At block 756, pulse characterization data representing the identified portions of the canonical seizure termination exceeding the threshold is generated. In some embodiments, this can include determining attributes of the pulses represented and/or defined by the pulse characterization data from the canonical seizure termination, and generating pulse characterization data based on these determined attributes. In some embodiments, these attributes can include, for example, pulse frequency, pulse amplitude, or pulse width. The pulse amplitude defined by the pulse characterization data can be determined based on the comparison of the threshold and the portions of the canonical seizure termination and/or waveform shape exceeding the threshold. Thus, in some embodiments, attributes of each portion of the canonical seizure termination and/or waveform shape exceeding the threshold can be identified. In some embodiments, an amplitude can be identified for some or all of the portions of the canonical seizure termination and/or waveform shape exceeding the threshold, and in some embodiments one or several pulse widths can be identified for some or all of the portions of the canonical seizure termination and/or waveform shape exceeding the threshold. In some embodiments, a pulse width is identified in the pulse characterization data for each pulse defined by the pulse characterization data.

In some embodiments, the amplitude for at least one pulse defined in the pulse characterization data and associated with the selected portion of the waveform varies proportionally to the amplitude of the associated portion of the canonical seizure termination and/or of the waveform shape of the threshold. In some embodiments, the amplitude for at least one pulse defined in the pulse characterization data and associated with the selected portion of the waveform varies proportionally to the difference between the threshold and the selected portion of the canonical seizure termination and/or of the waveform shape of the threshold. Thus, in such an embodiment, the amplitude of the pulse defined by the pulse characterization data increases as the difference between the threshold and the selected portion of the canonical seizure termination and/or of the waveform shape of the threshold increases and the amplitude of the pulse defined by the pulse characterization data decreases as the difference between the threshold and the selected portion of the canonical seizure termination and/or of the waveform shape of the threshold decreases.

Similarly, in some embodiments, the width of the pulse defined by the pulse characterization data can vary proportionally to a width of the portion of the waveform shape and/or portion of the canonical seizure termination associated with that pulse and that exceeds the threshold and/or proportionally to the duration of the portion of the waveform shape and/or of the canonical seizure termination associated with that pulse and exceeding the threshold.

In some embodiments, the attributes of the pulse(s) defined by the pulse characterization data can relate to aspects of the waveform shape and/or to aspects of the canonical seizure termination. In some embodiments, for example, this relation can be a proportional relationship, and in some embodiments, this relationship can be non-proportional such as a relationship achieved via a non-linear transfer function. In some embodiments, the amplitude of the pulse can be characterized as a continuous value or discretely/incrementally. In such embodiments in which the amplitude of the pulse is characterized discretely/incrementally, the amplitude of a pulse can comprise one or a finite number of discrete and predetermined amplitudes. In some embodiments, the pulses defined by the pulse characterization data can comprise one or several biphasic pulses, and in some embodiments, some or all of the pulses defined by the pulse characterization data can be non-biphasic pulses.

After the generation of the pulse characterization data, the process 750 proceeds to block 758, and returns to block 706 of FIG. 7.

Figure 11:
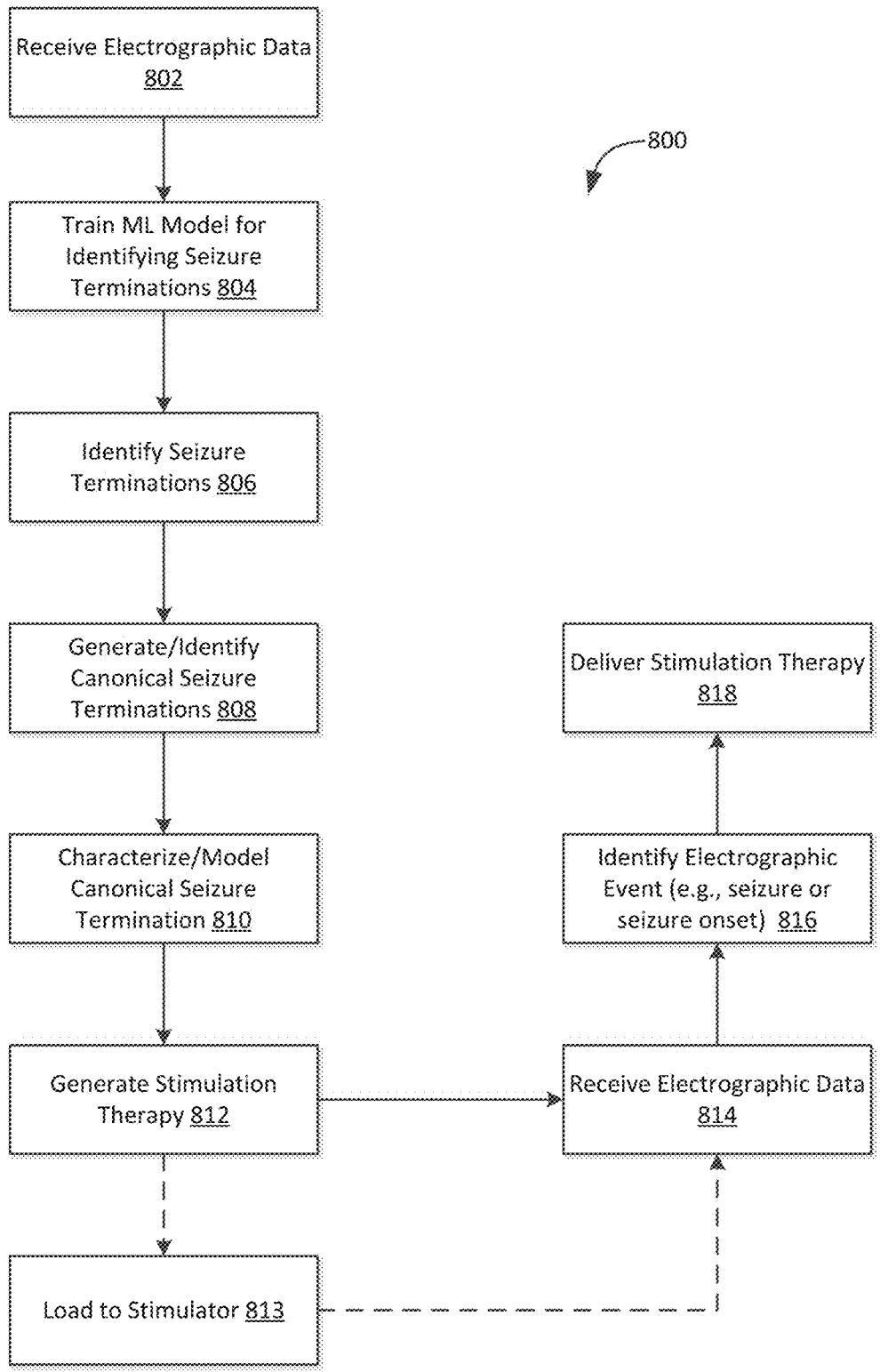
FIG. 11 is a flowchart illustrating a process according to embodiments for optimizing a neuromodulation therapy using stimulation mimicking seizure termination.

With reference now to FIG. 11, a flowchart illustrating one embodiment of a process 800 for defining a stimulation therapy is shown. The process 800 can be performed by neurostimulator 110 and/or the programmer 252. The process begins at block 802 wherein electrographic data for one or several patients is received. In some embodiments, the step of block 802 comprises receiving electrographic data relating to one electrographic seizure, and in some embodiments, the step of block 802 comprises receiving electrographic data over an extended period of time, which electrographic data can relate to a plurality of electrographic seizures. In some embodiments, the electrographic data is received by the detection subsystem 326 of the neurostimulator 110 and/or by the programmer 252. The electrographic data can comprise time-series data which can be raw time-series data gathered from some or all of the plurality of electrodes 312, 314, 316, and 318 of the neurostimulator 110.

The electrographic data can include data relating to a plurality of electrographic seizures. This can include, for example, all or portions of seizure onsets, evolutions, and offsets. In some embodiments, all or portions of the electrographic data can relate to electrographic seizures naturally terminating or terminating after electrical stimulation has been applied, albeit unsuccessfully, as an intervention.

In some embodiments, the electrographic data can comprise one or more channels of raw time-series data. In some embodiments, the electrographic data can comprise one or more spectrograms, each obtained from one or more channels of raw time-series data. In some embodiments, the electrographic data can comprise one or more coherograms, each obtained from two or more channels of raw time-series data. In some embodiments, the time-series data can comprise one or several channels of data, and in some embodiments, the time-series data can comprise one or more channels of data that can be recorded as a local field potential voltage over time. In some embodiments, each channel of time-series data corresponds with data recorded from a different recording site than every other channel. Thus, in some embodiments, each channel of time-series data comprises unique data.

At block 804 of the process 800, one or several machine learning models are trained, and in some embodiments, these one or several machine learning models are trained to identify seizure terminations in the data, which seizure terminations can comprise patterns in the data. This training can be performed by the training module 610 using information from the memory 604 and/or from the data module 606.

In some embodiments, the training of the machine learning model can be performed with electrographic data for a first plurality of electrographic seizures, which electrographic data for the first plurality of electrographic seizures can comprise a training set of time series data. The training set can characterize a first plurality of electrographic seizures in one or several patients. The machine learning model may be trained by applying a deep learning model to electrographic data corresponding to the first plurality of electrographic seizures to extract features from that data and provide a multi-dimensional feature vector. A clustering algorithm, such as k-means clustering, may then be applied to the feature vectors provided by the deep learning model to identify one or several clusters of electrographic seizures.

Feature extraction and clustering may involve the types of deep learning models and clustering algorithms described previously in this disclosure.

At block 806 one or several seizure terminations are identified in electrographic data characterizing electrographic seizures of at least one patient. In some embodiments, these one or several seizure terminations are identified in electrographic data gathered from a plurality of electrographic seizures from one or more patients by the machine learning model trained in block 804. In some embodiments, this electrographic data can characterize a second plurality of electrographic seizures—the training set characterizing a first plurality of electrographic seizures. In some embodiments, the first plurality of electrographic seizures and the second plurality of electrographic seizures can be exclusive such that data corresponding to an electrographic seizure is only represented in one of the training set or the electrographic data characterizing the second plurality of seizures. In some embodiments, the training set at least partially overlaps with the electrographic data characterizing the second plurality of seizures. In some embodiments, the identifying of seizure terminations includes ingesting the electrographic data characterizing the second plurality of electrographic seizures into the machine learning model, and receiving the output of the machine learning model, which output can comprise the identified seizure terminations. In some embodiments, the seizure terminations can be identified by the offset module 612.

Figure 16A:
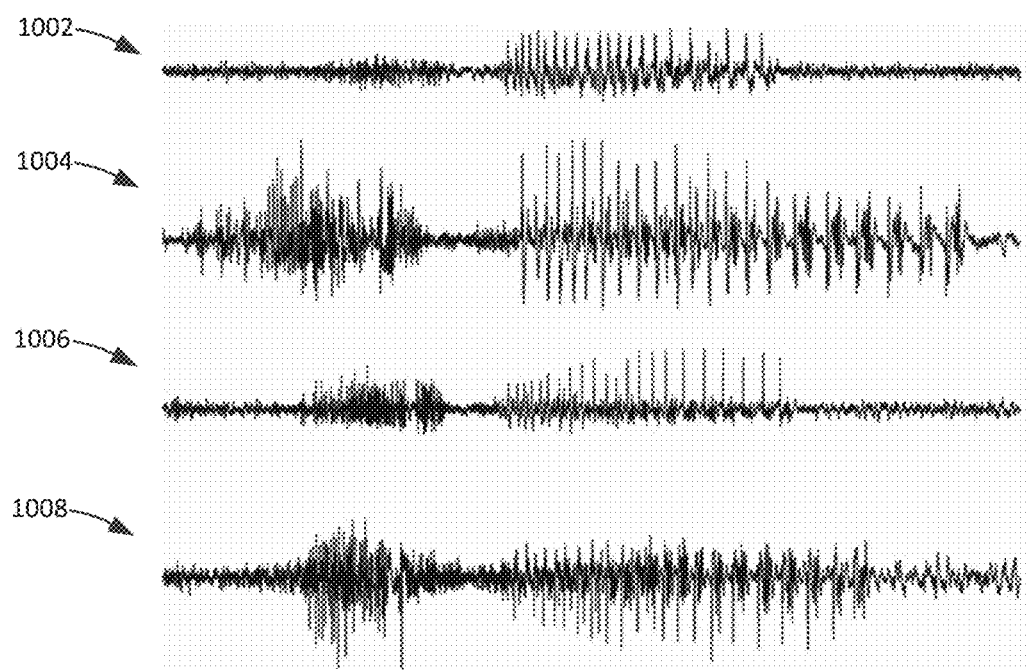
FIGS. 16A-16D graphically depict electrographic signals of seizure terminations (FIG. 16A), a canonical seizure termination (FIG. 16B) derived from the seizure terminations, a characterization or model (FIG. 16C) derived from the canonical seizure termination, and a stimulation therapy (FIG. 16D) derived from the characterization or model.

FIG. 16A depicts a set of example seizure terminations 1002, 1004, 1006, 1008 that may be identified in block 806. Each seizure termination 1002, 1004, 1006, 1008 may be sensed from the same sensing channel, at different times.

At block 808, a canonical seizure termination is generated and/or identified from the seizure block 806. In some embodiments, the canonical seizure termination comprises a pattern in time-series data, which pattern can be represented in an electrographic signal. In some embodiments, this pattern of the canonical seizure termination can comprise a single pattern representative of multiple seizure terminations identified from the time series data characterizing the second plurality of electrographic seizures. In some embodiments, the canonical seizure termination can be generated by the simulation module 614 and specifically by the ending generator 616.

Figures 14, 15:
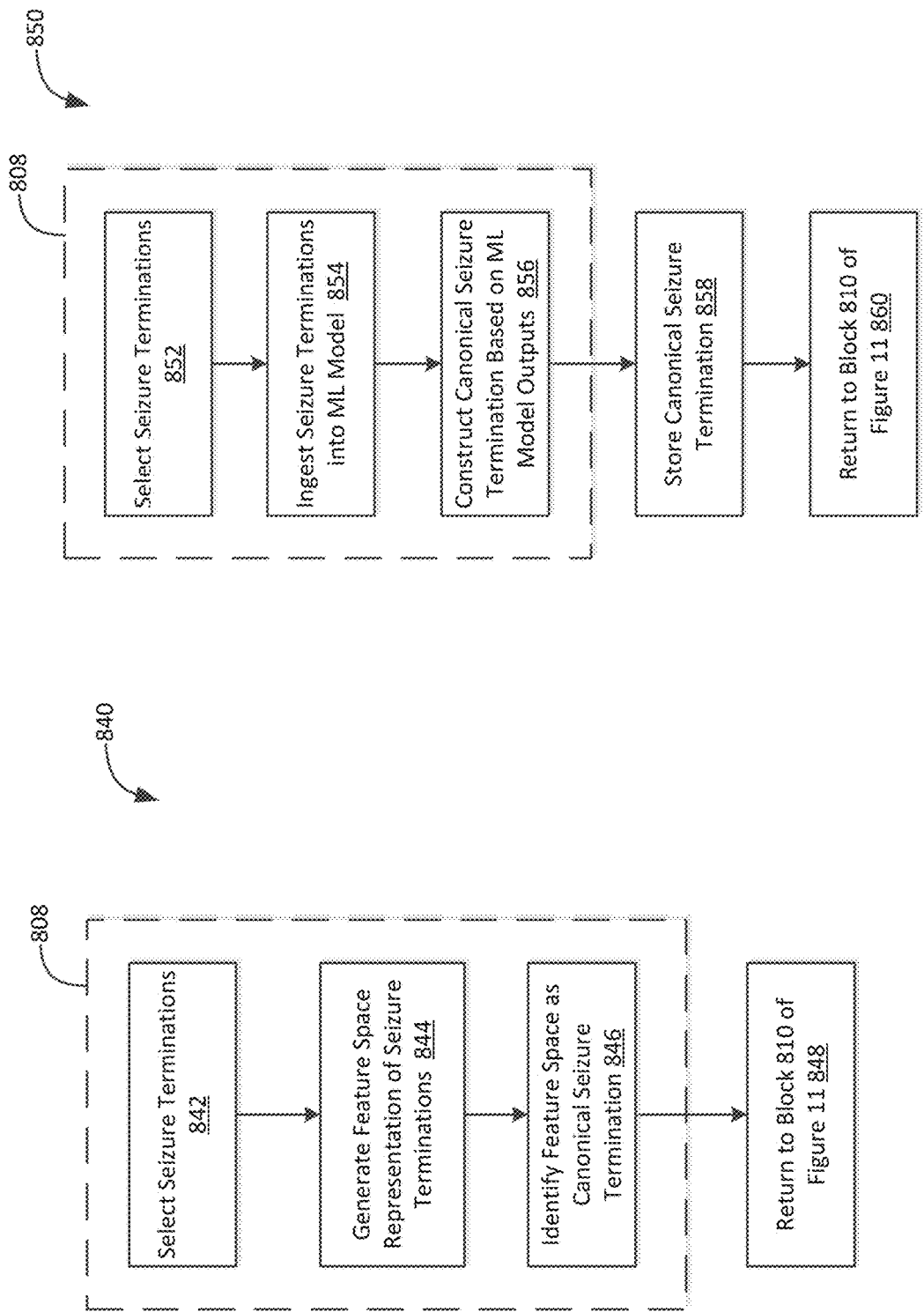
FIG. 14 is a flowchart illustrating a process according to embodiments for identifying and/or generating a canonical seizure termination based on a feature space representation.
FIG. 15 is a flowchart illustrating a process for identifying and/or generating a canonical seizure termination according to a machine learning model.
Figure 16B:
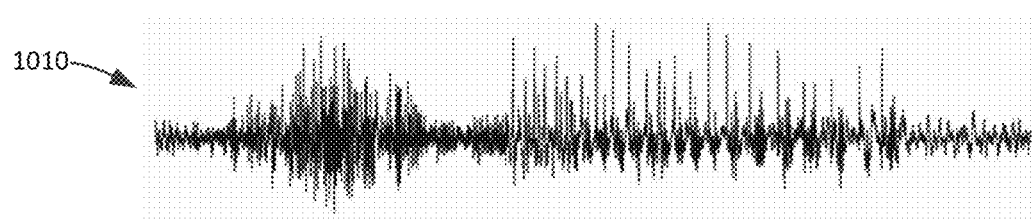

FIG. 16B depicts an example canonical seizure termination 1010 derived from the seizure terminations 1002, 1004, 1006, 1008 that may be generated in block 808. As disclosed in general above and in detail below with reference to FIGS. 13, 14 and 15, this canonical seizure termination can be generated via, for example, one or several of: averaging; dynamic time warping; or use of a machine learning model trained to generate a canonical seizure termination based on ingested seizure termination data. The amplitude of the canonical seizure termination 1010 may be subsequently scaled by some scaling factor when charactering it for purpose of translating it into a stimulation therapy.

At block 810 the canonical seizure termination identified and/or generated in block 808 is characterized and/or modeled. In some embodiments, the characterizing and/or modeling of the canonical seizure termination identified and/or generated in block 808 can be performed by the simulation module 614 and specifically by the modeling engine 618 in the simulation module 614. In some embodiments, the characterizing and/or modeling of the canonical seizure termination can include the applying of the electrographic signal representing the pattern of the canonical seizure termination to the modeling engine 618, which modeling engine can be an analyzer, and determining, with the modeling engine 618, a waveform shape characterizing the pattern of the canonical seizure termination. Although block 810 specifically references modeling of the seizure terminations, in some embodiments, the entire seizure, such as an entire canonical electrographic seizure, can be modeled, and the portion of the modeled seizure corresponding to the seizure termination can be identified as the canonical seizure termination. In embodiments in which the entire seizure is modeled, this modeling can include the determining of a canonical seizure in a manner similar to the step of block 808.

Figure 16C:

FIG. 16C depicts an example characterizing and/or modeling 1012 of the canonical seizure termination 1010 that may be generated in block 810. Each of the upward ticks from the horizontal line corresponds to a voltage (or current) that would be applied as part of a stimulation therapy.

At block 812, a stimulation therapy is generated. In some embodiments, the stimulation therapy can be generated to approximate all or portions of the canonical seizure termination and/or the pattern or waveform shape characterizing the pattern of the canonical seizure termination. In some embodiments, this can include the generation of a stimulation therapy having one or several frequencies common with the waveform representative of the pattern of the canonical seizure termination and/or extracted from the waveform representative of the canonical seizure termination. In some embodiments, the generation of the stimulation therapy can include the generation of one or several pulses for delivery to the patient, which one or several pulses share attributes with the identified canonical seizure termination. These shared attributes can include, for example, pulse frequency, pulse amplitude, or pulse width. In some embodiments, the first stimulation therapy can be associated with the first seizure type, and can be stored in the memory 604. In some embodiments, the generation of the stimulation therapy can include the steps of process 750 of FIG. 10. Although depicted as separate steps, in some embodiments, some or all of blocks 808 through 812 are combined into a single step.

In some embodiments, these pulses can have one or several attributes that can be fixed and/or variable. In some embodiments, these attributes can include, for example, pulse frequency, pulse spacing, pulse amplitude, and/or pulse width. In some embodiments, the pulse amplitude can be fixed, and in some embodiments, the pulse amplitude can be variable. In some embodiments, the pulse width can be fixed, and in some embodiments, the pulse width can be variable. In embodiments in which the pulse amplitude is variable, the pulse amplitude can vary in relation to one or several attributes of the canonical seizure termination including, for example, the amplitude of the waveform shape characterizing the canonical seizure termination. In some embodiments, the pulse amplitude varies between discrete incremental amplitude levels, and in some embodiments, the pulse amplitude is continuously variable.

In some embodiments, the generation of the stimulation therapy comprises generating pulse characterization data that can identify one or several pulses forming the stimulation therapy, and one or several attributes of these one or several pulses. In some embodiments, these one or several attributes can include, for example, a pulse timing within the stimulation therapy, a pulse frequency, a pulse amplitude, and/or a pulse duration. In some embodiments, the pulse characterization data can be translated by the therapy subsystem 328 into one or several pulses that can be delivered to the patient. In some embodiments, the generation of pulse characterization includes discretizing the canonical seizure termination, comparing a value associated with each of the discrete portions of the canonical seizure termination to a threshold, and generating pulse characterization data defining a pulse based on comparing the value associated with one of the discrete portions of the canonical seizure termination to the threshold.

Figure 16D:
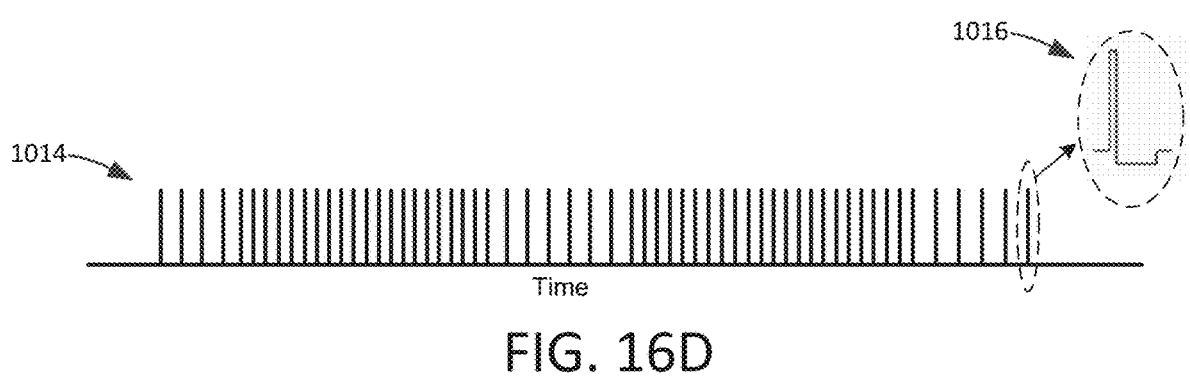

FIG. 16D depicts an example stimulation therapy 1014 generated in block 812. The stimulation therapy 1014 includes a delivery of a series of biphasic pulses 1016, spaced apart in time in accordance with the upward ticks of the corresponding modeling 1012 of the canonical seizure termination. Further details of the generation of the pulse characterization data can be found in process 750 of FIG. 10 and/or in process 820 of FIG. 12.

After the stimulation therapy has been generated, the process 800, if being performed by the programmer 252, can proceed to block 813, wherein the stimulation therapy is loaded to the neurostimulator 110. In some embodiments, the loading of the stimulation therapy to the neurostimulator 110 comprises updating software of the neurostimulator 110 with the stimulation therapy. As discussed above, the programmer 252 is a component that is distinct from the neurostimulator 110 (the neurostimulator being implantable and the programmer being external), but information can be downloaded to the programmer 252 from the neurostimulator 110, and information can be downloaded to the neurostimulator 110 from the programmer 252. In some embodiments, downloading of information to the neurostimulator 110 and/or to the programmer 252 can be performed using the wand discussed above.

After the stimulation therapy has been downloaded to the neurostimulator 110, or in the event that blocks 802 through 812 are performed by the neurostimulator 110, after completion of block 812, the process 800 proceeds to block 814, wherein electrographic data is received. In some embodiments, this electrographic data can be received as part of monitoring of the patient's electrographic activity with the implanted neurostimulator 110. In some embodiments, the electrographic data can be received by the detection subsystem 326 from one or several of the electrodes 312, 314, 316, 318.

After the electrographic data has been received, the process 800 proceeds to block 816, wherein an electrographic event is identified, and specifically wherein an electrographic seizure is identified. In some embodiments, the electrographic seizure can be identified via, for example, the detection subsystem 326 from the electrographic data received in block 814. In some embodiments, the electrographic seizure can be identified based on detection of one or several features within the received electrographic data.

After the electrographic event has been identified, the process 800 proceeds to block 818 wherein a stimulation therapy is delivered. In some embodiments, the stimulation therapy is delivered by the therapy subsystem 328 via one or several of the electrodes 312, 314, 316, 318. In some embodiments, delivering of the stimulation therapy comprises generating one or several pulses in the delivery of those one or several pulses to the patient.

Figure 12:
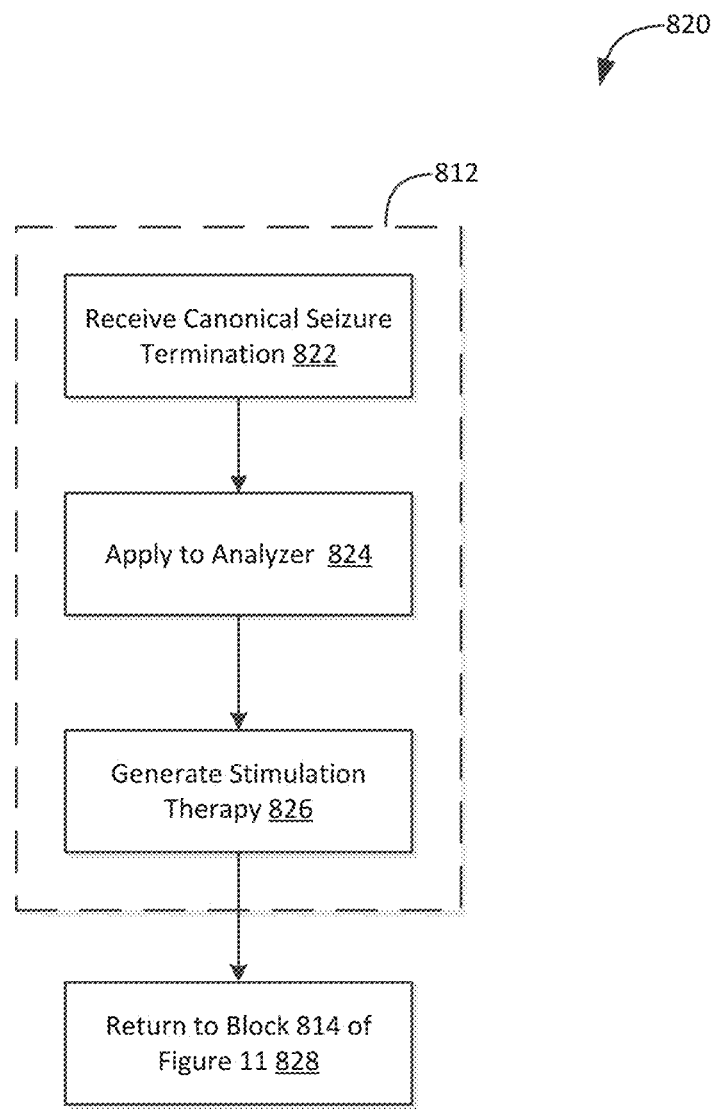
FIG. 12 is a flowchart illustrating a process according to embodiments for creating a stimulation therapy based on a canonical seizure termination.

With reference now to FIG. 12, a flowchart illustrating one embodiment of a process 820 for generating a stimulation therapy is shown. The process 820 can be performed as a part of, or in the place of the step of block 812 of FIG. 11. The process 820 begins at block 822, wherein a canonical seizure termination is received, which canonical seizure termination is a pattern in time-series data represented in an electrographic signal. In some embodiments, the canonical seizure termination is received by the modeling engine 618 from the ending generator 616 and/or from the memory 604. At block 824, the canonical seizure termination received in block 822 can be applied to an analyzer, which analyzer can be a part of the modeling engine. In some embodiments, the analyzer can determine a waveform shape that characterizes the pattern of the canonical seizure termination. In some embodiments, the analyzer can be or include the machine learning model trained to generate and/or determine the waveform shape characterizing the pattern of the canonical seizure termination. This machine learning model can be, for example, at least one of: a clustering algorithm; a classifier; a shallow neural network model; a deep neural network model; a hidden Markov model; or a recurrent neural network model; or any combination thereof, such as, for example, a long short-term memory (LSTM) neural network.

At block 826 a stimulation therapy is generated. In some embodiments, the waveform shape characterizing the stimulation therapy that mimics the canonical seizure termination generated and/or determined in block 824 can be provided to the therapy generator 620 from the memory 604 and/or from the modeling engine. In some embodiments, a stimulation delivered according to the stimulation therapy emulates all or portions of the canonical seizure termination such that a stimulation therapy at least partially emulates electrographic activity that occurs when the patient's seizures terminate naturally. The stimulation therapy can be generated by the stimulation module 614.

In some embodiments, generating the stimulation therapy includes creating pulse characterization data based on the canonical seizure termination. This pulse characterization data can identify one or several pulses forming the stimulation therapy, and one or several attributes of one, some, or all of these one or several pulses. In some embodiments, these one or several attributes can include, for example, a pulse timing within the stimulation therapy, a pulse frequency, a pulse amplitude, and/or a pulse duration. In some embodiments, the pulse characterization data can be translated, by the therapy subsystem 328, into one or several pulses that can be delivered to the patient. In some embodiments, the generation of the stimulation therapy can include the steps of process 750 of FIG. 10. After the generation of the stimulation therapy, the process 820 proceeds to block 828 and continues to block 814 of FIG. 11.

Figure 13:
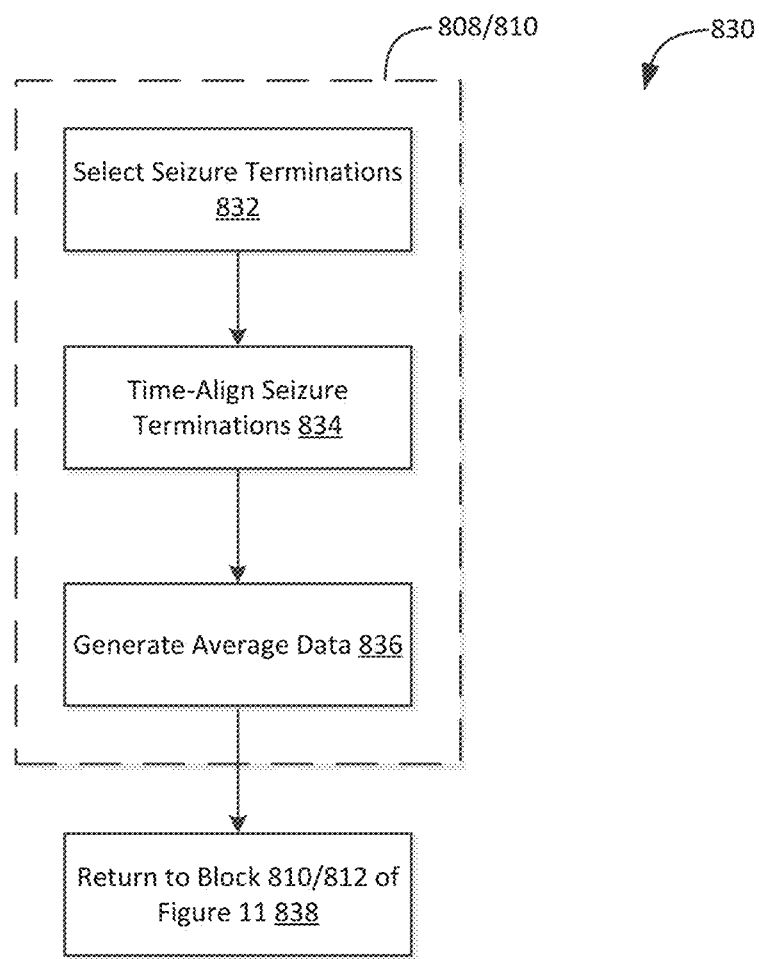
FIG. 13 is a flowchart illustrating a process according to embodiments for generating and/or identifying a canonical seizure termination.

With reference now to FIG. 13, a flowchart illustrating one embodiment of a process 830 for generating and/or identifying the canonical seizure termination is shown. The process 830 can be performed as a part of, or in the place of the step of block 808 and/or of blocks 808 and 810 of FIG. 11. In some embodiments, the process 830 is best applied when generating a canonical seizure termination characterizing a plurality of electrographic seizures of the same type. In some embodiments, the electrographic seizures are of the same type when they share sufficient common features and/or characteristics. In some embodiments, the process 830 becomes increasingly effective as the commonality between the data for the electrographic seizures increases.

The process can be performed by the simulation module 614, and specifically by the ending generator. The process 830 begins at block 832, wherein a plurality of seizure terminations are selected. The selected plurality of seizure terminations include multiple seizure terminations identified from the time-series data characterizing the second plurality of seizures. In some embodiments, the selected plurality of seizure terminations include all of the seizure terminations identified in the time-series data characterizing the second plurality of seizures. In some embodiments, these selected seizure terminations comprise some or all of the terminations of a type of seizure of one or several patients. In some embodiments, selecting the plurality of seizure terminations includes retrieving the electrographic data associated with the selected offsets from the offset module 612 and/or from the memory 604.

Figure 17A:
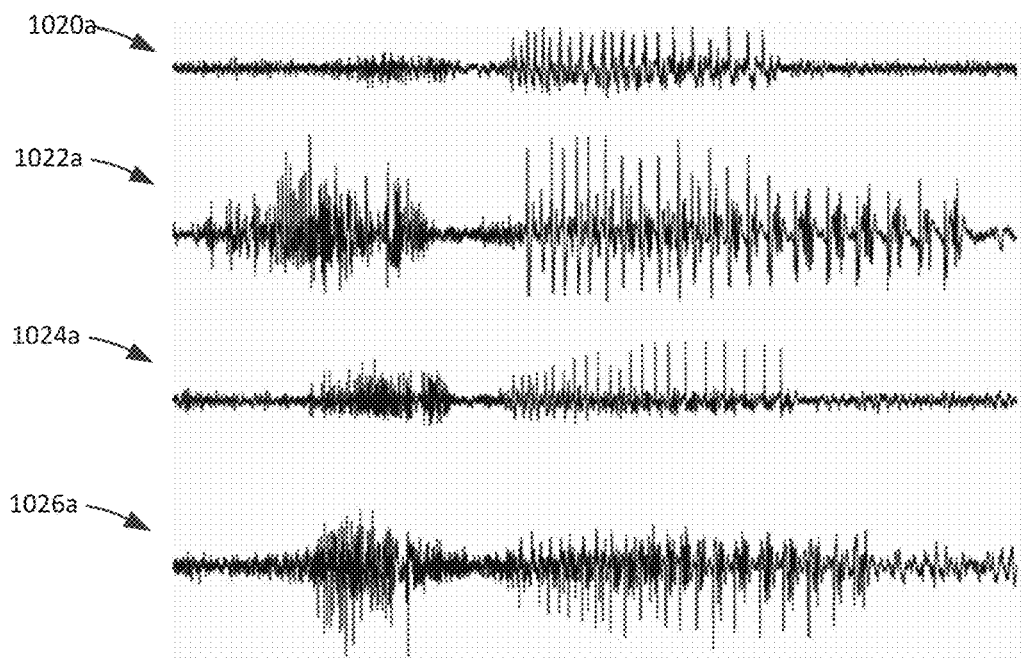
FIGS. 17A-17C graphically depict electrographic signals of seizure terminations (FIG. 17A), time-aligned versions of the electrographic signals of seizure terminations (FIG. 17B), and a canonical seizure termination (FIG. 17C) derived from the time-aligned seizure terminations.

FIG. 17A depicts a set of example seizure terminations 1020a, 1022a, 1024a, 1026a that may be identified in block 806. Each seizure termination 1020a, 1022a, 1024a, 1026a may be sensed from the same sensing channel, at different times. In other examples, each seizure in a set of seizures may be sensed and recorded from multiple channels simultaneously.

After the seizure terminations have been selected, the process 830 proceeds to block 834, wherein the selected seizure terminations are time-aligned using dynamic time warping. In some embodiments, the time aligning of the selected seizure terminations include shifting one or several time-related attributes of the time-series data of the selected seizure terminations. In some embodiments, this includes compressing or expanding the time-series data, truncating a portion of the time-series data, shifting the start of the time-series data, or the like. In some embodiments, for example, the start point of one or several selected offsets can be shifted to improve alignment of waveforms, features, and/or events in the offsets. Similarly, one or several seizure terminations can be compressed or expanded to improve alignment of waveforms, features, and/or events in the terminations. The amount of compression and/or expansion can vary along each example of an electrographic seizure. This is the "dynamic" part of dynamic time warping, an algorithm that automatically computes the best mapping from one signal to another by figuring out the best way to expand/contract each part of the first signal to map it onto the second signal.

Figure 17B:
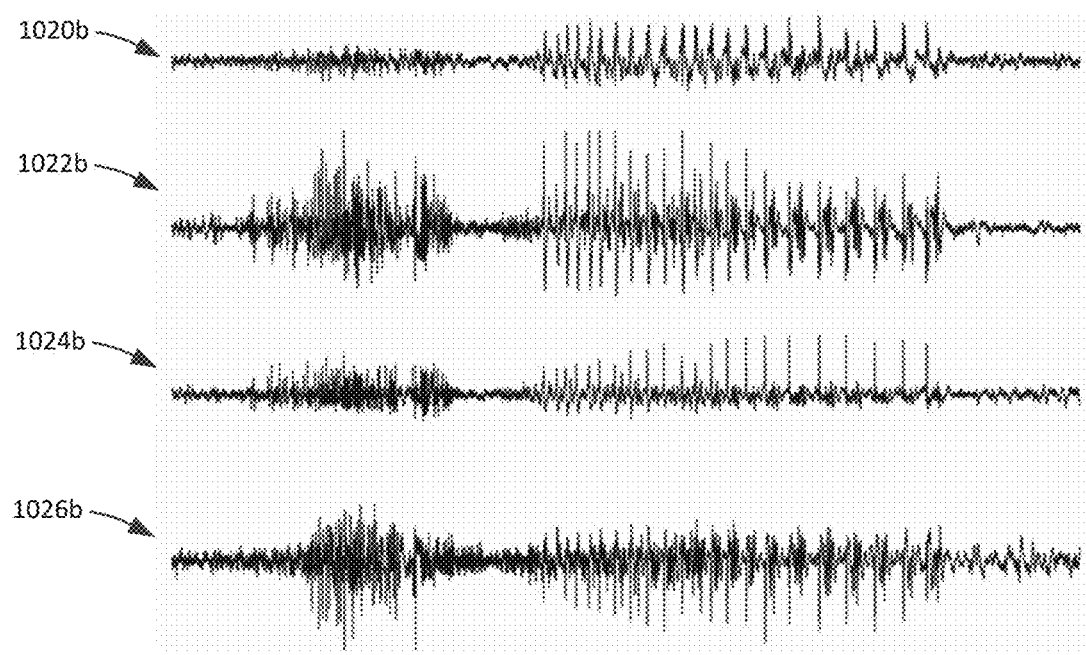

FIG. 17B depicts a set of time-aligned seizure terminations 1020b, 1022b, 1024b, 1026b corresponding to the set of example seizure terminations 1020a, 1022a, 1024a, 1026a shown in FIG. 17A.

After the seizure terminations have been time aligned, an average time-aligned seizure termination is generated for the time-aligned multiple selected seizure terminations as indicated in block 836 by taking their mean, median, or some other statistic that transforms multiple examples into a single canonical representation. In some embodiments, this includes selecting a time point in the selected seizure terminations, determining the voltage value at the time point in each of the selected seizure terminations, averaging the voltage values of the common time points in each of the selected seizure terminations, and assigning the average value to a time point in the time-series data of the canonical seizure termination corresponding with the time point in the selected seizure terminations. In some embodiments, this averaging is repeated for time points of the selected seizure terminations until the process for identifying the canonical seizure termination is complete, or until average voltage values have been identified for all of the time points and/or for a desired number of time points. The average data can be stored in the memory 604. After the average data has been generated, the process 830 proceeds to block 838 and continues to block 810 of FIG. 11 when the process 830 is performed in the place of block 808, or in embodiments in which the process 830 is performed in place of blocks 808 and 810, the process 830 proceeds to block 812 of FIG. 11.

Figure 17C:
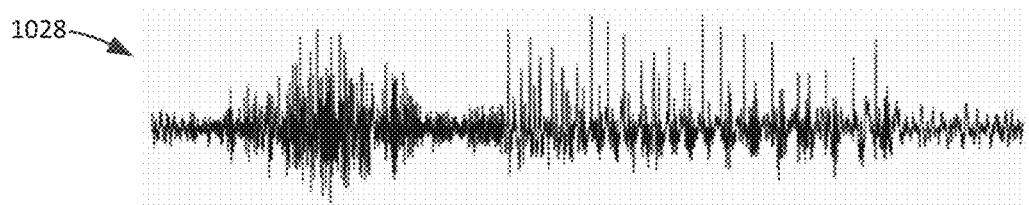

FIG. 17C depicts a single canonical representation 1028 resulting from averaging the set of time-aligned seizure terminations 1020b, 1022b, 1024b, 1026b shown in FIG. 17B.

With reference now to FIG. 14, a flowchart illustrating one embodiment of a process 840 for an embodiment of generating and/or identifying a canonical seizure termination is determined. The process 840 can be performed as a part of, or in the place of, the step of blocks 808 and 810 of FIG. 11. The process can be performed by the simulation module 614, and specifically by the ending generator 616. The process 840 begins at block 842, wherein a plurality of seizure terminations are selected. The step of block 842 can be the same as the step of block 832. In some embodiments, the selection of the plurality of seizure terminations can include the retrieval of the electrographic data associated with the selected terminations from the offset module 612 and/or from the memory 604.

After the plurality of seizure terminations are selected, the process 840 proceeds to block 844, wherein a high-level feature space representation of the multiple seizure terminations is generated. In some embodiments, this includes identifying features in each of the selected plurality of seizure terminations. Feature vectors can be generated from these features. In some embodiments, a feature vector can be generated for each of the seizure terminations from the selected plurality of seizure terminations. The feature vector of a seizure termination can be generated with features identified in that termination. The feature vectors can be generated by a machine learning model, which can, based on the ingested seizure terminations, provide an output. In some embodiments, this output can be a multi-dimensional feature vector identifying features of a canonical seizure termination, and/or in some embodiments, this output can be time-series electrographic data forming the canonical seizure termination. In some embodiments, the features are obtained from a middle layer of a multi-layer neural network. In some embodiments, the machine learning model may comprise any combination of a classifier, a hidden Markov model, a decision tree, a neural network model including a shallow convolutional neural network, deep convolutional neural network, and/or recurrent neural network. In some embodiments, the machine learning model can be a recurrent neural network containing a deep learning architecture such as, for example, a long short-term memory network. In some embodiments, the machine learning model can be an auto-encoder or a generative model.

After the feature space representation of the seizure terminations has been generated, the process 840 proceeds to block 846, wherein the high-level feature space representation is visualized in the same low-level feature space as the original electrographic data, and the latter is identified as the canonical seizure termination. In some embodiments in which the machine learning model is an auto-encoder or a generative model, the output of the machine learning model is the canonical seizure termination. The stimulation therapy can be extracted from this canonical seizure termination with block 812 of FIG. 11 and stored in, for example, the memory 604. After identifying the stimulation therapy, the process 840 proceeds to block 848 and continues with block 812 of FIG. 11. For example, with reference to FIGS. 17A and 17C, a machined learning model may be applied to the seizure terminations 1020a, 1022a, 1024a, 1026a to produce the canonical seizure termination 1028.

With reference now to FIG. 15, a flowchart illustrating one embodiment of a process 850 for an embodiment of generating and/or identifying a canonical seizure termination is shown. The process 850 can be performed as a part of, or in the place of, the step of block 808 of FIG. 11. The process can be performed by the simulation module 614, and specifically by the ending generator 616.

The process 850 begins at block 852, wherein a plurality of seizure terminations are selected. The step of block 852 can be the same as the step of block 832. In some embodiments, the selection of the plurality of seizure terminations can include the retrieval of the electrographic data associated with the selected seizure terminations from the offset module 612 and/or from the memory 604.

After the selecting of the seizure terminations, the process 850 proceeds to block 854, wherein the selected seizure terminations are ingested into a machine learning model. In some embodiments, the machine learning model can be trained to generate canonical seizure terminations based on ingested seizure terminations. In some embodiments, the step of block 854 can match the step of block 844. In some embodiments, the machine learning model can include functionalities enabling a visualization of activation of deep layers in terms of lower level features. In some embodiments, these functionalities can be obtained by the incorporation of the machine learning model into an auto-encoder and/or into a generative architecture.

At block 856, the output of the machine learning model is received and the canonical seizure termination is automatically constructed based on the outputs of the machine learning model. In some embodiments, the construction of the canonical seizure termination can be based, at least in part, on the visualization of the activation of the deep layers of the machine learning model in terms of its low-level features. After the canonical seizure termination has been constructed, the process 850 proceeds to block 858, wherein the canonical seizure termination is stored. In some embodiments, the canonical seizure termination can be stored in the memory 604. For example, with reference to FIGS. 17A and 17C, a machined learning model may be applied to the seizure terminations 1020b, 1022b, 1024b, 1026b to produce the canonical seizure termination 1028. After the canonical seizure termination has been stored, the process 850 proceeds to block 860 and continues to block 810 of FIG. 11.

U.S. Pat. No. 10,252,056 to Mogul proposes stimulating the brain with a frequency that is determined by the coherence frequency at seizure termination. For reasons set forth below with reference to FIG. 18, Mogul's strategy of brain stimulation would work only for a small subset of seizures that have a single, clear frequency of peak coherence at seizure termination. As described further below, for example with reference to FIGS. 19 and 20, most seizures cannot be characterized that simply, and thus, specifying a single frequency for the stimulation (i.e. specifying a constant time interval between pulses) will not work for most types of seizures. Accordingly, instead of specifying a frequency of stimulation, the methods and systems disclosed herein propose to specify the timing of each individual pulse of a stimulation therapy by the discretization of the canonical seizure termination (and in one instantiation, both the timing and duration of each stimulation pulse). In another instantiation, the methods and systems disclosed herein propose to specify using the canonical seizure termination, without discretization, to prescribe the entire stimulation therapy. To this end, another way to prescribe a stimulation therapy is to map the canonical seizure termination directly to a stimulation therapy, for example, using the waveform of an entire canonical seizure termination to specify an entire stimulation therapy formed by a series of pulses, each characterized by a stimulation voltage or stimulation current.

Figure 18:
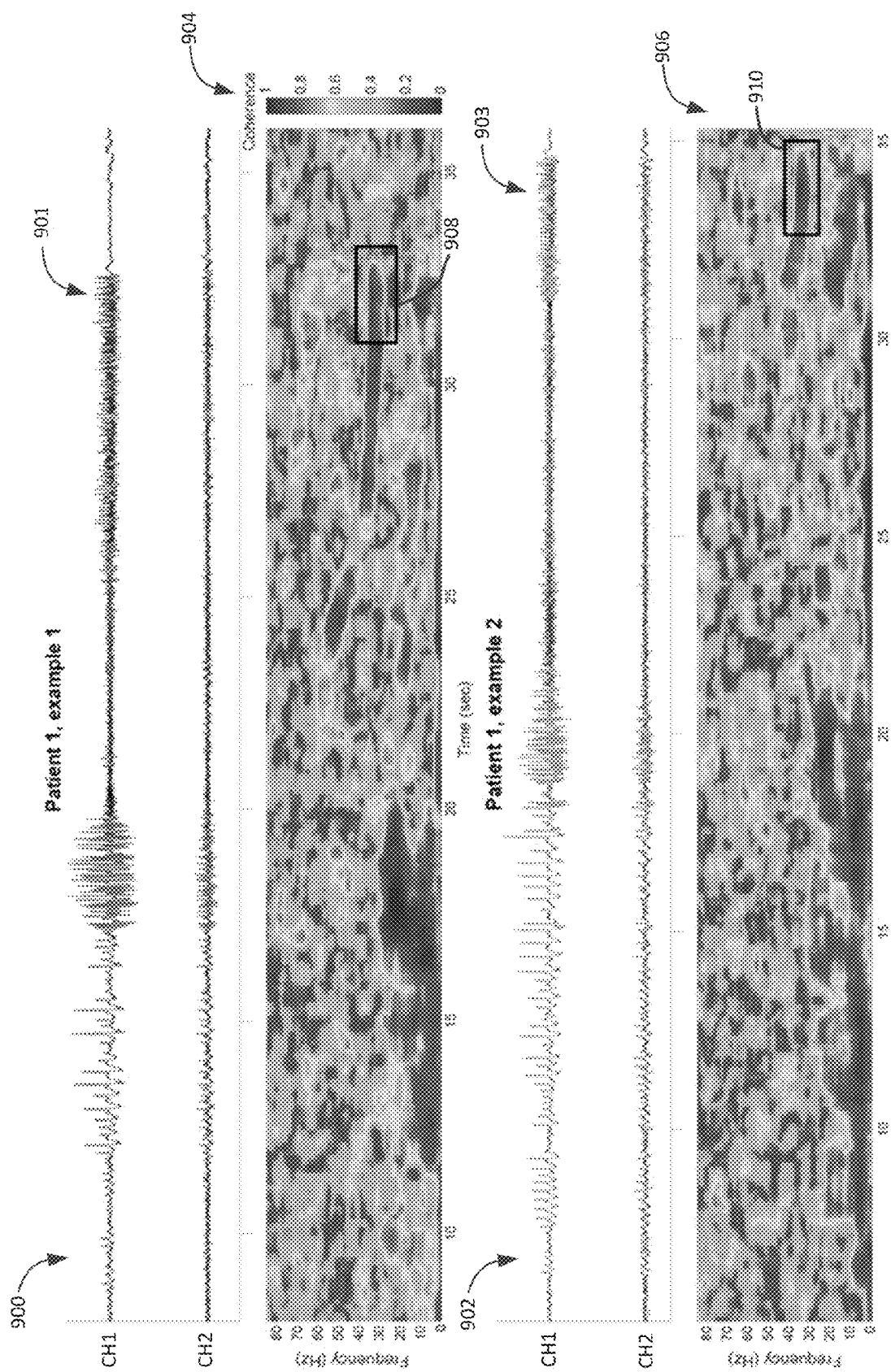
FIG. 18 graphically depicts electrographic signals evidencing seizure activity in a patient on both a voltage versus time plot and a spectrogram.

FIG. 18 depicts two data sets for a single patient, and specifically two sets of electrographic data taken during the two electrographic seizures. The first of these data sets is identified as Patient 1, example 1 and the second of these data sets is identified as Patient 1, example 2. Both the first and second data sets include time series data 900, 902 for two channels and a coherogram 904, 906 exhibiting a time-frequency profile of the coherence across the two channels. As seen in FIG. 18, both the first and second examples show similarities in the shape of the electrographic data 900, 902, and as seen in the coherograms 904, 906, both of the seizure offsets are also characterized by a similar peak in coherence of around 32 Hz. This similar peak in coherence is identified by boxes 908, 910, at the offset period 901, 903 of the electrographic seizure.

Figure 19:
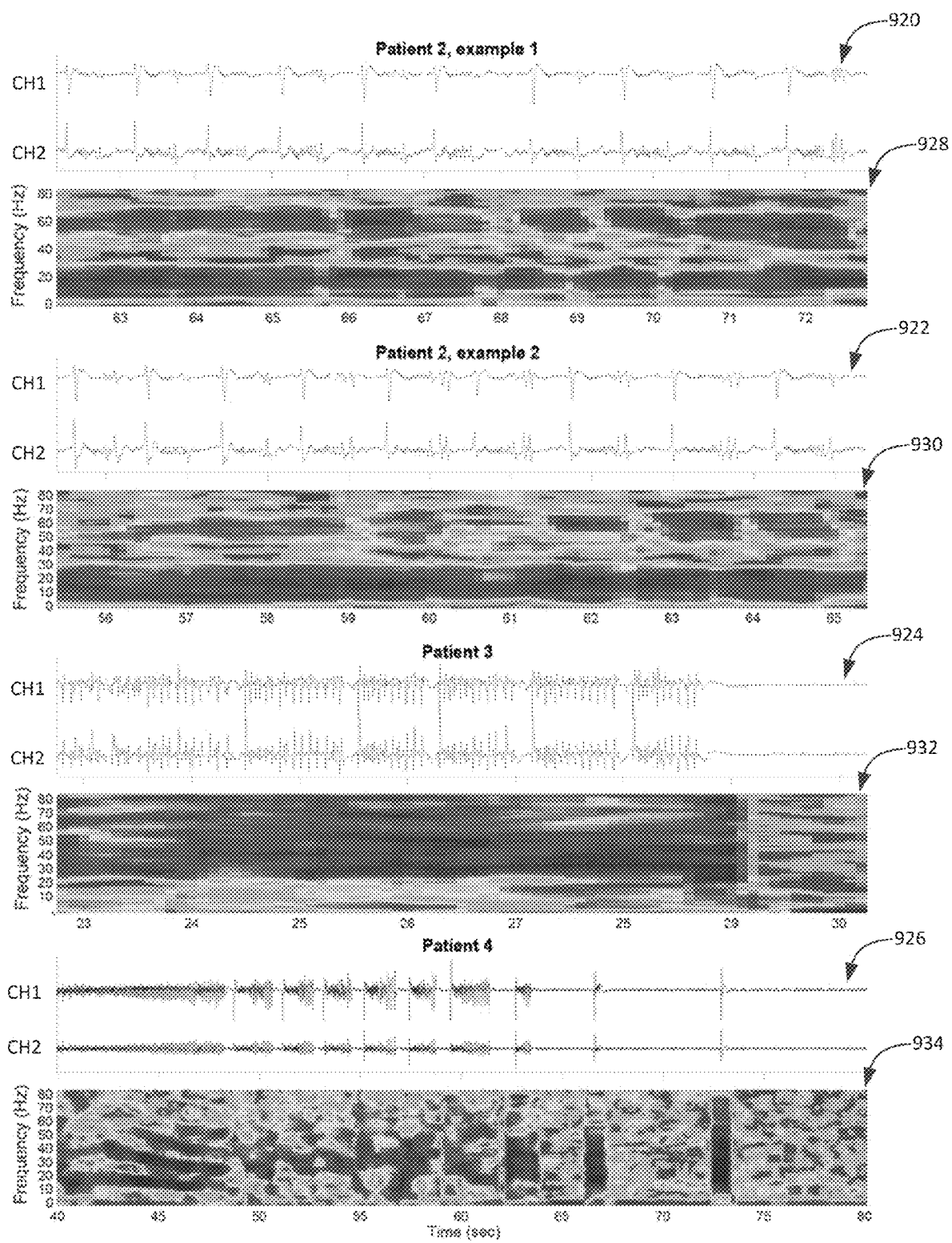
FIG. 19 graphically depicts electrographic signals evidencing seizure activity in different patients on both a voltage versus time plot and a spectrogram.

FIG. 19 depicts four sets of data taken from three patients, and specifically four sets of electrographic data taken during the seizure offset of four different electrographic seizures. The first of these data sets is identified as Patient 2, example 1; the second of these data sets is identified as Patient 2, example 2; the third of these data sets is identified as Patient 3; and the fourth of these data sets is identified as Patient 4. Each of these data sets includes time series data 920, 922, 924, 926 for the two channels and a coherogram 928, 930, 932, 934 exhibiting a coherence profile of the coherence across the two channels. As seen in FIG. 19, both the first and second examples for Patient 2 show similarities in the shape of the electrographic data 920, 922, and both have high coherence, but in contrast to the examples of FIG. 18, there is not a dominant peak in coherence. The data for Patients 3 and 4 both exhibit "chirp" patterns, with the "chirps" in the data of Patient 4 decreasing their duration and increasing their spacing over time. Neither the data of Patient 3 nor the data of Patient 4 exhibits a clear coherency peak.

Figure 20:
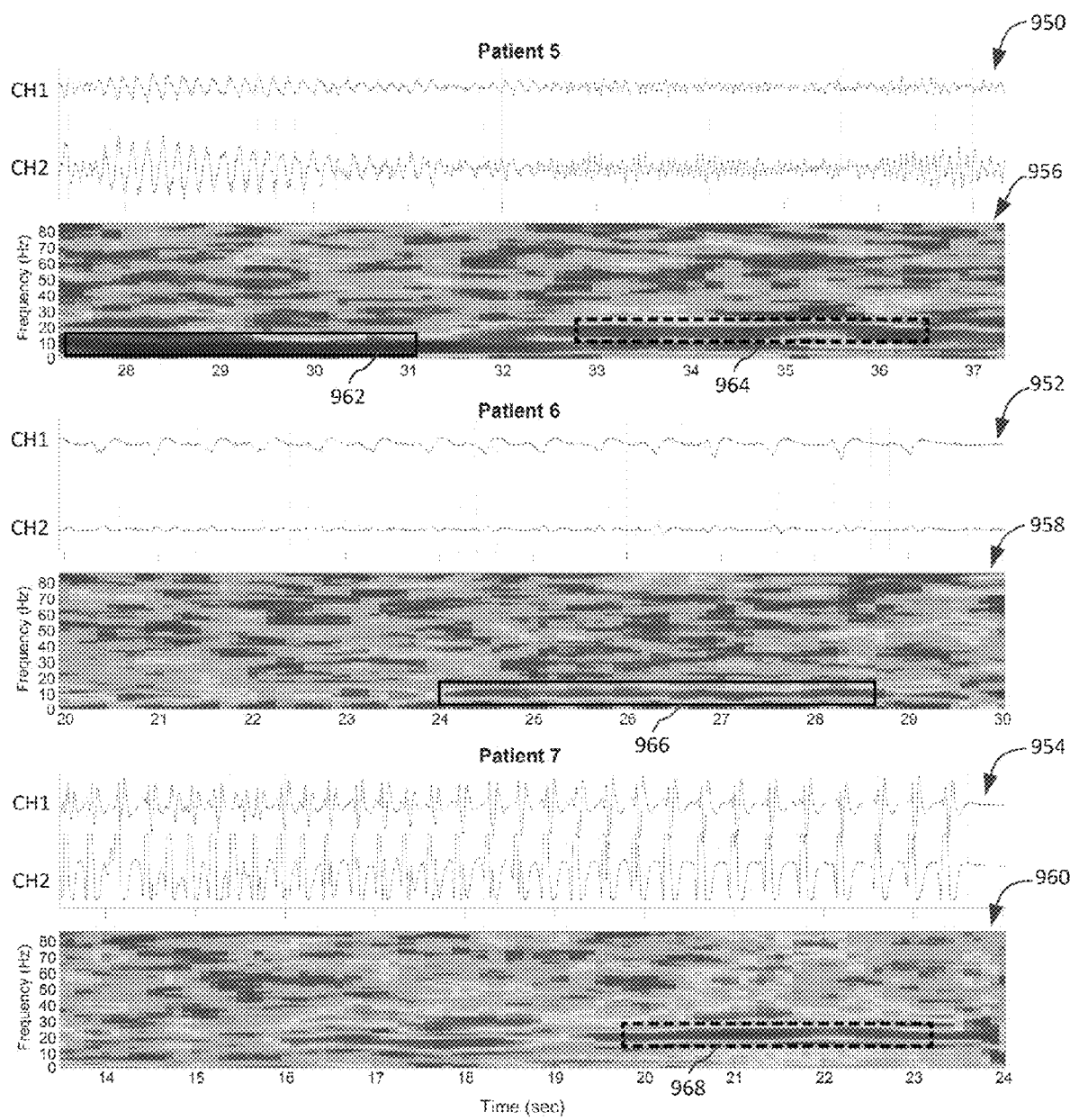
FIG. 20 graphically depicts data corresponding to multiple patients processed according to embodiments.

FIG. 20 depicts three sets of data taken from three patients, and specifically three sets of electrographic data taken during seizure offset for three different electrographic seizures. The first of these data sets is identified as Patient 5, the second of these data sets is identified as Patient 6, and the third of these data sets is identified as Patient 7. Each of these data sets includes time series data 950, 952, 954 for two channels and a coherogram 956, 958, 960 exhibiting a profile of the coherence at different frequencies and time points across the two channels. As seen in FIG. 20, Patient 5's time series data 950 shows similarities between the two channels, and the coherogram 956 quantifies these similarities as a high level of coherence near 8 Hz from 28-31 sec (box 962) and near 20 Hz from 33-36 sec. (box 964). Patient 6's time series data 952 shows few similarities with Patient 5's time series data from 28-31 sec., but the coherogram, like Patient 5's coherogram, shows a high level of coherence of around 8 Hz (box 966). Similarly, Patient 7's time series data 954 shows relatively few similarities to Patient 5's time-series data from 33-36 sec. (Patient 5's dashed box); however, the coherogram 960 shows a high level of coherence around 20 Hz (box 968).

Thus, summarizing the data from FIGS. 18, 19, and 20, seizure offset data collected from different patients may share one or several coherence frequencies even when the time series data differ across the same patients. Thus, one or several common coherence frequencies may not adequately capture the seizure offset as, even in instances with similar coherence frequencies, the time series data from the different patients may be drastically different. In other words, there is no clear correspondence between coherence and seizure termination, and coherence is insufficient to fully characterize seizure terminations.

Figure 21A:
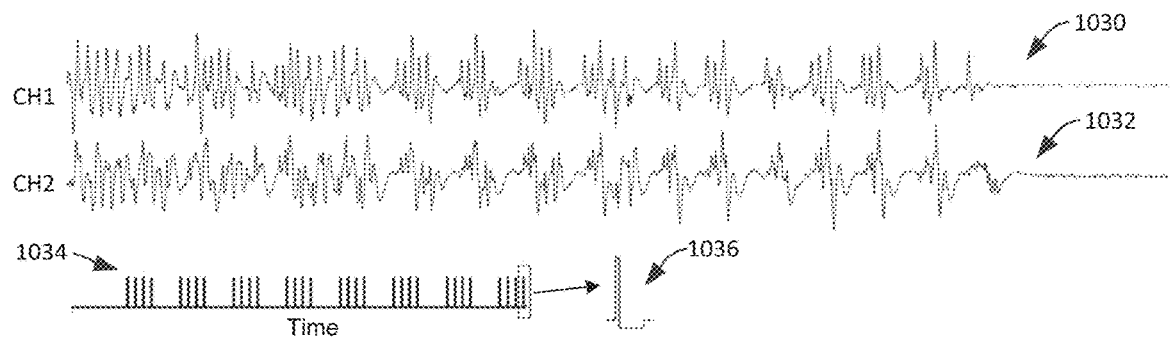
FIGS. 21A-21C graphically depict three pairs of canonical seizure terminations derived from the seizure terminations, and a stimulation therapy derived from the pair of canonical seizure terminations.
Figure 21B:
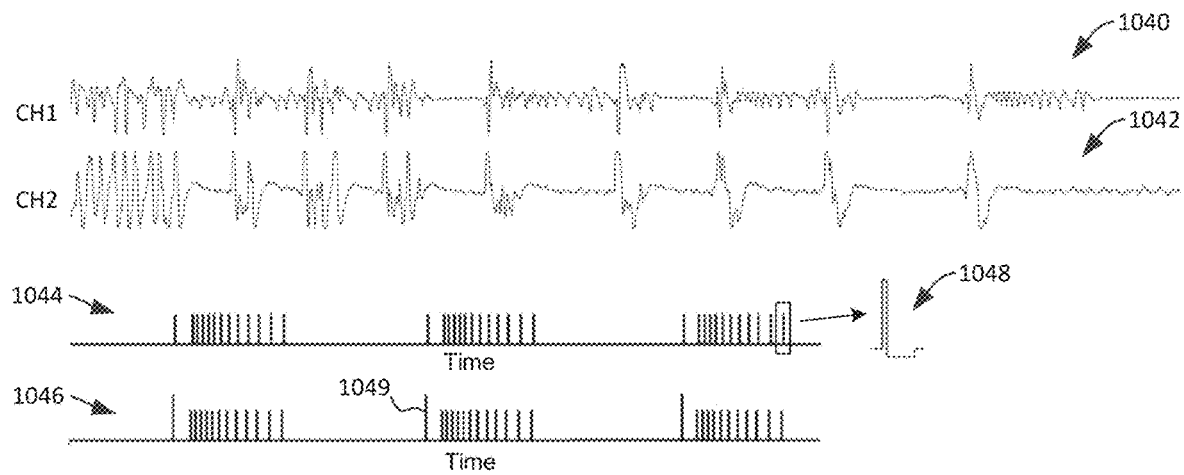
Figure 21C:
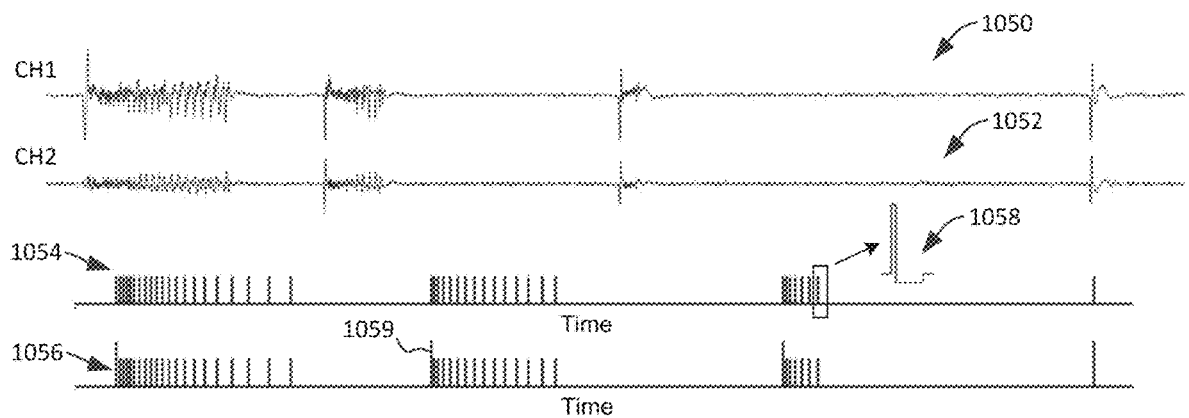

FIGS. 21A, 21B and 21C each depict an example pair of canonical seizure terminations and an example stimulation pattern that may be derived for the canonical seizure terminations in accordance with embodiments disclosed herein. Each canonical seizure termination in a pair is based on an electrographic signal sensed from a different channel. Thus, each pair represents canonical seizure terminations resulting from a same seizure event.

In FIG. 21A, each canonical seizure termination 1030, 1032 is derived from an approximate 10 second, time-series electrographic signal sensed simultaneously in the hippocampal region of the brain of a first patient and spanning the end of a hippocampal seizure. The canonical seizure terminations 1030, 1032 consist of several bursts, with the amplitude of the higher frequency oscillation, e.g., approximately 12 Hz, in each burst being modulated by the phase of a lower-frequency oscillation, e.g., approximately 2 Hz. The stimulation pattern 1034 comprises a bursts of pulses 1036 separated by an interval. The stimulation pattern 1034 mimics the frequency profile of the pair of canonical seizure terminations 1030, 1032.

In FIG. 21B, each canonical seizure termination 1040, 1042 is derived from an approximate 10 second, time-series electrographic signal sensed simultaneously in the hippocampal region of the brain of a second patient and spanning the end of a hippocampal seizure. The canonical seizure terminations 1040, 1042 have a frequency pattern more complex the canonical seizure terminations of FIG. 21A, and have a continuous progression of higher to lower frequencies (a "chirp") within each burst, and with chirps alternating with periods of suppression between spikes. Two example stimulation patterns 1044, 1046 comprise a bursts of pulses 1048 separated by an interval, with each burst having a series of pulses with an interpulse interval that increases. These stimulation patterns 1044, 1046 mimic the frequency profile of the pair of canonical seizure terminations 1040, 1042. In the second stimulation pattern 1046, the amplitude of the first pulse 1049 in each burst of pulses may be scaled to more closely mimic the amplitudes of the waveforms in the canonical seizure terminations 1040, 1042.

In FIG. 21C, each canonical seizure termination 1050, 1052 is derived from an approximate 15 second, time-series electrographic signal sensed simultaneously in the hippocampal region of the brain of a third patient and spanning the end of a hippocampal seizure. The canonical seizure terminations 1050, 1052 have a continuous progression of higher to lower frequencies (a "chirp") within each burst, and with chirps alternating with periods of suppression between spikes. Relative to the chirps in FIG. 21B, the chirps in FIG. 21C are shorter and further apart in time until they disappear. Two example stimulation patterns 1054, 1056 comprise a bursts of pulses 1058 separated by an interval, with each burst having a series of pulses with an interpulse interval that increases. These stimulation patterns 1054, 1056 mimic the frequency profile of the pair of canonical seizure terminations 1050, 1052. In the second stimulation pattern 1056, the amplitude of the first pulse 1059 in each burst of pulses may be scaled to more closely mimic the amplitudes of the waveforms in the canonical seizure terminations 1050, 1052.

A number of variations and modifications of the disclosed embodiments can be used. Specific details are given in the above description to provide a thorough understanding of the embodiments. However, it is understood that the embodiments may be practiced without these specific details. For example, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be rearranged, steps can be added to the processes in addition to steps shown in the flow diagrams, and/or one or more steps may be removed from processes shown in the flow diagrams. Unless otherwise noted in the specification, no step shown in the flow diagrams is essential. Although depicted as separate figures, steps from different flowcharts can be combined together. Further, a process is terminated when its operations are completed, but the process could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine-readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine-readable mediums for storing information. The term "machine-readable medium" includes, but is not limited to, portable or fixed storage devices, optical storage devices, and/or various other storage mediums capable of storing that contain or carry instruction(s) and/or data.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of neurostimulation, the method comprising:
    detecting an instance of an electrographic seizure based on a patient's electrographic activity, wherein the electrographic seizure is characterized by an offset; and
    responsive to a detection of an instance of the electrographic seizure, delivering a stimulation therapy to the patient, wherein the stimulation therapy emulates a canonical seizure offset constructed from a plurality of seizure offsets in electrographic seizures.

2. The method of claim 1, wherein detecting an instance of an electrographic seizure based on a patient's electrographic activity comprises applying a machine learning model to the patient's electrographic activity.

3. The method of claim 2, wherein the electrographic seizure is characterized by an onset, and the machine learning model is trained to detect the onset of the electrographic seizure.

4. The method of claim 2, wherein:
    the machine learning model is trained to identify a seizure type corresponding to the instance of the electrographic seizure; and
    the stimulation therapy emulates the canonical seizure offset corresponding to the identified seizure type.

5. The method of claim 2, wherein the machine learning model comprises one or more of a deep learning model, a clustering algorithm, a recurrent neural network, a hidden Markov model, a long short term memory neural network.

6. The method of claim 1, further comprising:
    creating the stimulation therapy that emulates the canonical seizure offset.

7. The method of claim 6, wherein creating the stimulation therapy that emulates the canonical seizure offset comprises creating pulse characterization data based on the canonical seizure offset.

8. The method of claim 7, wherein delivering a stimulation therapy to the patient comprises translating the pulse characterization data into a train of stimulation pulses.

9. The method of claim 1, wherein constructing the canonical seizure offset comprises applying a machine learning model to the plurality of seizure offsets in the electrographic seizures, wherein the machine learning model is trained to generate the canonical seizure offset based on ingested seizure offsets.

10. An implantable neurostimulator system for delivering a stimulation therapy, the system comprising:
    a plurality of electrodes;
    a detection module coupled to the plurality of electrodes, the detection module configured to detect an instance of an electrographic seizure based on a patient's electrographic activity, wherein the electrographic seizure is characterized by an offset; and
    a stimulation generator configured to deliver a stimulation therapy to the patient in response to a detection of an instance of the electrographic seizure, wherein the stimulation therapy emulates a canonical seizure offset constructed from a plurality of seizure offsets in electrographic seizures.

11. The implantable neurostimulator system of claim 10, wherein the detection module detects an instance of an electrographic seizure based on a patient's electrographic activity by being further configured to apply a machine learning model to the patient's electrographic activity.

12. The implantable neurostimulator system of claim 11, wherein the electrographic seizure is characterized by an onset, and the machine learning model is trained to detect the onset of the electrographic seizure.

13. The implantable neurostimulator system of claim 11, wherein:
    the machine learning model is trained to identify a seizure type corresponding to the instance of the electrographic seizure; and
    the stimulation therapy emulates a canonical seizure offset corresponding to the identified seizure type.

14. The implantable neurostimulator system of claim 11, wherein the machine learning model comprises one or more of a deep learning model, a clustering algorithm, a recurrent neural network, a hidden Markov model, a long short term memory neural network.

15. The implantable neurostimulator system of claim 10, wherein the stimulation therapy that emulates the canonical seizure offset comprises pulse characterization data that is based on the canonical seizure offset.

16. The implantable neurostimulator system of claim 15, wherein the stimulation generator is configured to translate the pulse characterization data into a train of stimulation pulses.

17. The implantable neurostimulator system of claim 10, wherein:
    the stimulation generator comprises a training module configured to construct the canonical seizure offset based on the plurality of seizure offsets in the electrographic seizures.

18. The implantable neurostimulator system of claim 17, wherein the training module is configured to construct the canonical seizure offset by being further configured to apply a machine learning model to the plurality of electrographic seizures, wherein the machine learning model is trained to generate the canonical seizure offset based on ingested seizure offsets.

19. The implantable neurostimulator system of claim 18, wherein the machine learning model comprises one or more of a deep learning model, a clustering algorithm, a recurrent neural network, a hidden Markov model, a long short term memory neural network.

* * * * *